(12) United States Patent
O'Connor et al.

(10) Patent No.: US 11,628,251 B2
(45) Date of Patent: Apr. 18, 2023

(54) ACTIVITY MODE FOR ARTIFICIAL PANCREAS SYSTEM

(71) Applicant: INSULET CORPORATION, Acton, MA (US)

(72) Inventors: Jason O'Connor, Acton, MA (US); Joon Bok Lee, Acton, MA (US); Trang Ly, Concord, MA (US); Todd Vienneau, Mississauga (CA); Yibin Zheng, Hartland, WI (US); Ashutosh Zade, San Diego, CA (US)

(73) Assignee: INSULET CORPORATION, Acton, MA (US)

( * ) Notice: Subject to any disclaimer, the term of this patent is extended or adjusted under 35 U.S.C. 154(b) by 868 days.

(21) Appl. No.: 16/586,440

(22) Filed: Sep. 27, 2019

(65) Prior Publication Data

US 2020/0101225 A1 Apr. 2, 2020

Related U.S. Application Data

(60) Provisional application No. 62/738,531, filed on Sep. 28, 2018.

(51) Int. Cl.
*A61M 5/172* (2006.01)
*A61K 38/28* (2006.01)
*A61M 5/142* (2006.01)

(52) U.S. Cl.
CPC ........... *A61M 5/1723* (2013.01); *A61K 38/28* (2013.01); *A61M 5/14248* (2013.01);
(Continued)

(58) Field of Classification Search
None
See application file for complete search history.

(56) References Cited

U.S. PATENT DOCUMENTS 303,013 A 8/1884 Horton
2,797,149 A 6/1957 Skeggs
(Continued)

FOREIGN PATENT DOCUMENTS

AU 2015200834 A1 3/2015
AU 2015301146 A1 3/2017
(Continued)

OTHER PUBLICATIONS

US 5,954,699 A, 09/1999, Jost et al. (withdrawn)
(Continued)

*Primary Examiner* — Manuel A Mendez
(74) *Attorney, Agent, or Firm* — Goodwin Procter LLP

(57) ABSTRACT

A wearable drug delivery device, techniques, and computer-readable media that provide an application that implements a diabetes treatment plan for a user are described. The drug delivery device may include a controller operable to direct operation of the wearable drug delivery device. The controller may provide a selectable activity mode of operation for the user. Operation of the drug delivery device in the activity mode of operation may reduce a likelihood of hypoglycemia during times of increased insulin sensitivity for the user and may reduce a likelihood of hyperglycemia during times of increased insulin requirements for the user. The activity mode of operation may be manually activated by the user or may be activated automatically by the controller. The controller may automatically activate the activity mode of operation based on a detected activity level of the user and/or a detected location of the user.

20 Claims, 6 Drawing Sheets

(52) U.S. Cl.
CPC ............. *A61M 2005/14252* (2013.01); *A61M 2205/18* (2013.01); *A61M 2205/3553* (2013.01); *A61M 2205/3584* (2013.01); *A61M 2205/502* (2013.01); *A61M 2205/52* (2013.01); *A61M 2230/201* (2013.01); *A61M 2230/63* (2013.01)

(56) References Cited

U.S. PATENT DOCUMENTS

| | | |
|---|---|---|
| 3,631,847 A | 1/1972 | Hobbs |
| 3,634,039 A | 1/1972 | Brondy |
| 3,812,843 A | 5/1974 | Wootten et al. |
| 3,841,328 A | 10/1974 | Jensen |
| 3,963,380 A | 6/1976 | Thomas, Jr. et al. |
| 4,055,175 A | 10/1977 | Clemens et al. |
| 4,146,029 A | 3/1979 | Ellinwood, Jr. |
| 4,151,845 A | 5/1979 | Clemens |
| 4,245,634 A | 1/1981 | Albisser et al. |
| 4,368,980 A | 1/1983 | Aldred et al. |
| 4,373,527 A | 2/1983 | Fischell |
| 4,403,984 A | 9/1983 | Ash et al. |
| 4,464,170 A | 8/1984 | Clemens et al. |
| 4,469,481 A | 9/1984 | Kobayashi |
| 4,475,901 A | 10/1984 | Kraegen et al. |
| 4,526,568 A | 7/1985 | Clemens et al. |
| 4,526,569 A | 7/1985 | Bernardi |
| 4,529,401 A | 7/1985 | Leslie et al. |
| 4,559,033 A | 12/1985 | Stephen et al. |
| 4,559,037 A | 12/1985 | Franetzki et al. |
| 4,573,968 A | 3/1986 | Parker |
| 4,624,661 A | 11/1986 | Arimond |
| 4,633,878 A | 1/1987 | Bombardieri |
| 4,657,529 A | 4/1987 | Prince et al. |
| 4,685,903 A | 8/1987 | Cable et al. |
| 4,731,726 A | 3/1988 | Allen, III |
| 4,743,243 A | 5/1988 | Vaillancourt |
| 4,755,173 A | 7/1988 | Konopka et al. |
| 4,781,688 A | 11/1988 | Thoma et al. |
| 4,781,693 A | 11/1988 | Martinez et al. |
| 4,808,161 A | 2/1989 | Kamen |
| 4,854,170 A | 8/1989 | Brimhall et al. |
| 4,886,499 A | 12/1989 | Cirelli et al. |
| 4,900,292 A | 2/1990 | Berry et al. |
| 4,919,596 A | 4/1990 | Slate et al. |
| 4,925,444 A | 5/1990 | Orkin et al. |
| 4,940,527 A | 7/1990 | Kazlauskas et al. |
| 4,975,581 A | 12/1990 | Robinson et al. |
| 4,976,720 A | 12/1990 | Machold et al. |
| 4,981,140 A | 1/1991 | Wyatt |
| 4,994,047 A | 2/1991 | Walker et al. |
| 5,007,286 A | 4/1991 | Malcolm et al. |
| 5,097,834 A | 3/1992 | Skrabal |
| 5,102,406 A | 4/1992 | Arnold |
| 5,109,850 A | 5/1992 | Blanco et al. |
| 5,125,415 A | 6/1992 | Bell |
| 5,134,079 A | 7/1992 | Cusack et al. |
| 5,153,827 A | 10/1992 | Coutre et al. |
| 5,165,406 A | 11/1992 | Wong |
| 5,176,662 A | 1/1993 | Bartholomew et al. |
| 5,178,609 A | 1/1993 | Ishikawa |
| 5,207,642 A | 5/1993 | Orkin et al. |
| 5,232,439 A | 8/1993 | Campbell et al. |
| 5,237,993 A | 8/1993 | Skrabal |
| 5,244,463 A | 9/1993 | Cordner, Jr. et al. |
| 5,257,980 A | 11/1993 | Van Antwerp et al. |
| 5,273,517 A | 12/1993 | Barone et al. |
| 5,281,808 A | 1/1994 | Kunkel |
| 5,299,571 A | 4/1994 | Mastrototaro |
| 5,308,982 A | 5/1994 | Ivaldi et al. |
| 5,342,298 A | 8/1994 | Michaels et al. |
| 5,377,674 A | 1/1995 | Kuestner |
| 5,380,665 A | 1/1995 | Cusack et al. |
| 5,385,539 A | 1/1995 | Maynard |
| 5,389,078 A | 2/1995 | Zalesky et al. |
| 5,411,889 A | 5/1995 | Hoots et al. |
| 5,421,812 A | 6/1995 | Langley et al. |
| 5,468,727 A | 11/1995 | Phillips et al. |
| 5,505,709 A | 4/1996 | Funderburk et al. |
| 5,505,828 A | 4/1996 | Wong et al. |
| 5,507,288 A | 4/1996 | Bocker et al. |
| 5,533,389 A | 7/1996 | Kamen et al. |
| 5,558,640 A | 9/1996 | Pfeiler et al. |
| 5,569,186 A | 10/1996 | Lord et al. |
| 5,584,813 A | 12/1996 | Livingston et al. |
| 5,609,572 A | 3/1997 | Lang |
| 5,665,065 A | 9/1997 | Colman et al. |
| 5,678,539 A | 10/1997 | Schubert et al. |
| 5,685,844 A | 11/1997 | Marttila |
| 5,685,859 A | 11/1997 | Komerup |
| 5,693,018 A | 12/1997 | Kriesel et al. |
| 5,697,899 A | 12/1997 | Hillman et al. |
| 5,700,695 A | 12/1997 | Yassinzadeh et al. |
| 5,703,364 A | 12/1997 | Rosenthal |
| 5,714,123 A | 2/1998 | Sohrab |
| 5,716,343 A | 2/1998 | Kriesel et al. |
| 5,722,397 A | 3/1998 | Eppstein |
| 5,741,228 A | 4/1998 | Lambrecht et al. |
| 5,746,217 A | 5/1998 | Erickson et al. |
| 5,755,682 A | 5/1998 | Knudson et al. |
| 5,758,643 A | 6/1998 | Wong et al. |
| 5,800,405 A | 9/1998 | McPhee |
| 5,800,420 A | 9/1998 | Gross et al. |
| 5,801,057 A | 9/1998 | Smart et al. |
| 5,804,048 A | 9/1998 | Wong et al. |
| 5,817,007 A | 10/1998 | Fodgaard et al. |
| 5,820,622 A | 10/1998 | Gross et al. |
| 5,823,951 A | 10/1998 | Messerschmidt |
| 5,840,020 A | 11/1998 | Heinonen et al. |
| 5,848,991 A | 12/1998 | Gross et al. |
| 5,851,197 A | 12/1998 | Marano et al. |
| 5,858,005 A | 1/1999 | Kriesel |
| 5,865,806 A | 2/1999 | Howell |
| 5,871,470 A | 2/1999 | McWha |
| 5,879,310 A | 3/1999 | Sopp et al. |
| 5,902,253 A | 5/1999 | Pfeiffer et al. |
| 5,931,814 A | 8/1999 | Alex et al. |
| 5,932,175 A | 8/1999 | Knute et al. |
| 5,935,099 A | 8/1999 | Peterson et al. |
| 5,947,911 A | 9/1999 | Wong et al. |
| 5,971,941 A | 10/1999 | Simons et al. |
| 5,993,423 A | 11/1999 | Choi |
| 5,997,501 A | 12/1999 | Gross et al. |
| 6,017,318 A | 1/2000 | Gauthier et al. |
| 6,024,539 A | 2/2000 | Blomquist |
| 6,032,059 A | 2/2000 | Henning et al. |
| 6,036,924 A | 3/2000 | Simons et al. |
| 6,040,578 A | 3/2000 | Malin et al. |
| 6,049,727 A | 4/2000 | Crothall |
| 6,050,978 A | 4/2000 | Orr et al. |
| 6,058,934 A | 5/2000 | Sullivan |
| 6,066,103 A | 5/2000 | Duchon et al. |
| 6,071,292 A | 6/2000 | Makower et al. |
| 6,072,180 A | 6/2000 | Kramer et al. |
| 6,077,055 A | 6/2000 | Vilks |
| 6,090,092 A | 7/2000 | Fowles et al. |
| 6,101,406 A | 8/2000 | Hacker et al. |
| 6,102,872 A | 8/2000 | Doneen et al. |
| 6,115,673 A | 9/2000 | Malin et al. |
| 6,123,827 A | 9/2000 | Wong et al. |
| 6,124,134 A | 9/2000 | Stark |
| 6,126,637 A | 10/2000 | Kriesel et al. |
| 6,128,519 A | 10/2000 | Say |
| 6,142,939 A | 11/2000 | Eppstein et al. |
| 6,143,164 A | 11/2000 | Heller et al. |
| 6,157,041 A | 12/2000 | Thomas et al. |
| 6,161,028 A | 12/2000 | Braig et al. |
| 6,162,639 A | 12/2000 | Douglas |
| 6,196,046 B1 | 3/2001 | Braig et al. |
| 6,200,287 B1 | 3/2001 | Keller et al. |
| 6,200,338 B1 | 3/2001 | Solomon et al. |
| 6,214,629 B1 | 4/2001 | Freitag et al. |
| 6,226,082 B1 | 5/2001 | Roe |
| 6,244,776 B1 | 6/2001 | Wiley |
| 6,261,065 B1 | 7/2001 | Nayak et al. |

(56) References Cited

U.S. PATENT DOCUMENTS

| | | |
|---|---|---|
| 6,262,798 B1 | 7/2001 | Shepherd et al. |
| 6,270,455 B1 | 8/2001 | Brown |
| 6,271,045 B1 | 8/2001 | Douglas et al. |
| 6,280,381 B1 | 8/2001 | Malin et al. |
| 6,285,448 B1 | 9/2001 | Kuenstner |
| 6,309,370 B1 | 10/2001 | Haim et al. |
| 6,312,888 B1 | 11/2001 | Wong et al. |
| 6,334,851 B1 | 1/2002 | Hayes et al. |
| 6,375,627 B1 | 4/2002 | Mauze et al. |
| 6,379,301 B1 | 4/2002 | Worthington et al. |
| 6,402,689 B1 | 6/2002 | Scarantino et al. |
| 6,470,279 B1 | 10/2002 | Samsoondar |
| 6,475,196 B1 | 11/2002 | Vachon |
| 6,477,901 B1 | 11/2002 | Tadigadapa et al. |
| 6,484,044 B1 | 11/2002 | Lilienfeld-Toal |
| 6,491,656 B1 | 12/2002 | Morris |
| 6,512,937 B2 | 1/2003 | Blank et al. |
| 6,525,509 B1 | 2/2003 | Petersson et al. |
| 6,528,809 B1 | 3/2003 | Thomas et al. |
| 6,540,672 B1 | 4/2003 | Simonsen et al. |
| 6,544,212 B2 | 4/2003 | Galley et al. |
| 6,546,268 B1 | 4/2003 | Ishikawa et al. |
| 6,546,269 B1 | 4/2003 | Kumik |
| 6,553,841 B1 | 4/2003 | Blouch |
| 6,554,798 B1 | 4/2003 | Mann et al. |
| 6,556,850 B1 | 4/2003 | Braig et al. |
| 6,558,351 B1 | 5/2003 | Steil et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,562,014 B2 | 5/2003 | Lin et al. |
| 6,569,125 B2 | 5/2003 | Jepson et al. |
| 6,572,542 B1 | 6/2003 | Houben et al. |
| 6,572,545 B2 | 6/2003 | Knobbe et al. |
| 6,574,490 B2 | 6/2003 | Abbink et al. |
| 6,575,905 B2 | 6/2003 | Knobbe et al. |
| 6,580,934 B1 | 6/2003 | Braig et al. |
| 6,618,603 B2 | 9/2003 | Varalli et al. |
| 6,633,772 B2 | 10/2003 | Ford et al. |
| 6,645,142 B2 | 11/2003 | Braig et al. |
| 6,653,091 B1 | 11/2003 | Dunn et al. |
| 6,662,030 B2 | 12/2003 | Khalil et al. |
| 6,669,663 B1 | 12/2003 | Thompson |
| 6,678,542 B2 | 1/2004 | Braig et al. |
| 6,699,221 B2 | 3/2004 | Vaillancourt |
| 6,718,189 B2 | 4/2004 | Rohrscheib et al. |
| 6,721,582 B2 | 4/2004 | Frepagnier et al. |
| 6,728,560 B2 | 4/2004 | Kollias et al. |
| 6,740,059 B2 | 5/2004 | Flaherty |
| 6,740,072 B2 | 5/2004 | Starkweather et al. |
| 6,751,490 B2 | 6/2004 | Esenaliev et al. |
| 6,758,835 B2 | 7/2004 | Close et al. |
| 6,780,156 B2 | 8/2004 | Haueter et al. |
| 6,810,290 B2 | 10/2004 | Lebel et al. |
| 6,837,858 B2 | 1/2005 | Cunningham et al. |
| 6,837,988 B2 | 1/2005 | Leong et al. |
| 6,846,288 B2 | 1/2005 | Nagar et al. |
| 6,862,534 B2 | 3/2005 | Sterling et al. |
| 6,865,408 B1 | 3/2005 | Abbink et al. |
| 6,890,291 B2 | 5/2005 | Robinson et al. |
| 6,936,029 B2 | 8/2005 | Mann et al. |
| 6,949,081 B1 | 9/2005 | Chance |
| 6,958,809 B2 | 10/2005 | Sterling et al. |
| 6,989,891 B2 | 1/2006 | Braig et al. |
| 6,990,366 B2 | 1/2006 | Say et al. |
| 7,008,404 B2 | 3/2006 | Nakajima |
| 7,009,180 B2 | 3/2006 | Sterling et al. |
| 7,016,713 B2 | 3/2006 | Gardner et al. |
| 7,018,360 B2 | 3/2006 | Flaherty et al. |
| 7,025,743 B2 | 4/2006 | Mann et al. |
| 7,025,744 B2 | 4/2006 | Utterberg et al. |
| 7,027,848 B2 | 4/2006 | Robinson et al. |
| 7,043,288 B2 | 5/2006 | Davis, III et al. |
| 7,060,059 B2 | 6/2006 | Keith et al. |
| 7,061,593 B2 | 6/2006 | Braig et al. |
| 7,096,124 B2 | 8/2006 | Sterling et al. |
| 7,115,205 B2 | 10/2006 | Robinson et al. |
| 7,128,727 B2 | 10/2006 | Flaherty et al. |
| 7,139,593 B2 | 11/2006 | Kavak et al. |
| 7,139,598 B2 | 11/2006 | Hull et al. |
| 7,144,384 B2 | 12/2006 | Gorman et al. |
| 7,171,252 B2 | 1/2007 | Scarantino et al. |
| 7,190,988 B2 | 3/2007 | Say et al. |
| 7,204,823 B2 | 4/2007 | Estes et al. |
| 7,248,912 B2 | 7/2007 | Gough et al. |
| 7,267,665 B2 | 9/2007 | Steil et al. |
| 7,271,912 B2 | 9/2007 | Sterling et al. |
| 7,278,983 B2 | 10/2007 | Ireland et al. |
| 7,291,107 B2 | 11/2007 | Hellwig et al. |
| 7,291,497 B2 | 11/2007 | Holmes et al. |
| 7,303,549 B2 | 12/2007 | Flaherty et al. |
| 7,303,622 B2 | 12/2007 | Loch et al. |
| 7,303,922 B2 | 12/2007 | Jeng et al. |
| 7,354,420 B2 | 4/2008 | Steil et al. |
| 7,388,202 B2 | 6/2008 | Sterling et al. |
| 7,402,153 B2 | 7/2008 | Steil et al. |
| 7,404,796 B2 | 7/2008 | Ginsberg |
| 7,429,255 B2 | 9/2008 | Thompson |
| 7,460,130 B2 | 12/2008 | Salganicoff |
| 7,481,787 B2 | 1/2009 | Gable et al. |
| 7,491,187 B2 | 2/2009 | Van Den Berghe et al. |
| 7,500,949 B2 | 3/2009 | Gottlieb et al. |
| 7,509,156 B2 | 3/2009 | Flanders |
| 7,547,281 B2 | 6/2009 | Hayes et al. |
| 7,569,030 B2 | 8/2009 | Lebel et al. |
| 7,608,042 B2 | 10/2009 | Goldberger et al. |
| 7,651,845 B2 | 1/2010 | Doyle, III et al. |
| 7,680,529 B2 | 3/2010 | Kroll |
| 7,734,323 B2 | 6/2010 | Blomquist et al. |
| 7,766,829 B2 | 8/2010 | Sloan et al. |
| 7,785,258 B2 | 8/2010 | Braig et al. |
| 7,806,854 B2 | 10/2010 | Damiano et al. |
| 7,806,886 B2 | 10/2010 | Kanderian, Jr. et al. |
| 7,918,825 B2 | 4/2011 | OConnor et al. |
| 7,946,985 B2 | 5/2011 | Mastrototaro et al. |
| 7,972,296 B2 | 7/2011 | Braig et al. |
| 8,221,345 B2 | 7/2012 | Blomquist |
| 8,251,907 B2 | 8/2012 | Sterling et al. |
| 8,449,524 B2 | 5/2013 | Braig et al. |
| 8,452,359 B2 | 5/2013 | Rebec et al. |
| 8,454,576 B2 | 6/2013 | Mastrototaro et al. |
| 8,467,980 B2 | 6/2013 | Campbell et al. |
| 8,478,557 B2 | 7/2013 | Hayter et al. |
| 8,547,239 B2 | 10/2013 | Peallield et al. |
| 8,597,274 B2 | 12/2013 | Sloan et al. |
| 8,622,988 B2 | 1/2014 | Hayter |
| 8,810,394 B2 | 8/2014 | Kalpin |
| 9,061,097 B2 | 6/2015 | Holt et al. |
| 9,171,343 B1 | 10/2015 | Fischell et al. |
| 9,233,204 B2 | 1/2016 | Booth et al. |
| 9,486,571 B2 | 11/2016 | Rosinko |
| 9,579,456 B2 | 2/2017 | Budiman et al. |
| 9,743,224 B2 | 8/2017 | San Vicente et al. |
| 9,907,515 B2 | 3/2018 | Doyle, III et al. |
| 9,980,140 B1 | 5/2018 | Spencer et al. |
| 9,984,773 B2 | 5/2018 | Gondhalekar et al. |
| 10,248,839 B2 | 4/2019 | Levy et al. |
| 10,335,464 B1 | 7/2019 | Michelich et al. |
| 10,583,250 B2 | 3/2020 | Mazlish et al. |
| 10,737,024 B2 | 8/2020 | Schmid |
| 10,987,468 B2 | 4/2021 | Mazlish et al. |
| 11,197,964 B2 | 12/2021 | Sjolund et al. |
| 11,260,169 B2 | 3/2022 | Estes |
| 2001/0021803 A1 | 9/2001 | Blank et al. |
| 2001/0034023 A1 | 10/2001 | Stanton, Jr. et al. |
| 2001/0034502 A1 | 10/2001 | Moberg et al. |
| 2001/0051377 A1 | 12/2001 | Hammer et al. |
| 2001/0053895 A1 | 12/2001 | Vaillancourt |
| 2002/0010401 A1 | 1/2002 | Bushmakin et al. |
| 2002/0010423 A1 | 1/2002 | Gross et al. |
| 2002/0016568 A1 | 2/2002 | Lebel et al. |
| 2002/0040208 A1 | 4/2002 | Flaherty et al. |
| 2002/0123740 A1 | 9/2002 | Flaherty et al. |
| 2002/0128543 A1 | 9/2002 | Leonhardt |

(56) References Cited

U.S. PATENT DOCUMENTS

| | | |
|---|---|---|
| 2002/0147423 A1 | 10/2002 | Burbank et al. |
| 2002/0155425 A1 | 10/2002 | Han et al. |
| 2002/0161288 A1 | 10/2002 | Shin et al. |
| 2003/0023148 A1 | 1/2003 | Lorenz et al. |
| 2003/0050621 A1 | 3/2003 | Lebel et al. |
| 2003/0060692 A1 | 3/2003 | L. Ruchti et al. |
| 2003/0086074 A1 | 5/2003 | Braig et al. |
| 2003/0086075 A1 | 5/2003 | Braig et al. |
| 2003/0090649 A1 | 5/2003 | Sterling et al. |
| 2003/0100040 A1 | 5/2003 | Bonnecaze et al. |
| 2003/0130616 A1 | 7/2003 | Steil et al. |
| 2003/0135388 A1 | 7/2003 | Martucci et al. |
| 2003/0144582 A1 | 7/2003 | Cohen et al. |
| 2003/0163097 A1 | 8/2003 | Fleury et al. |
| 2003/0195404 A1 | 10/2003 | Knobbe et al. |
| 2003/0208113 A1 | 11/2003 | Mault et al. |
| 2003/0208154 A1 | 11/2003 | Close et al. |
| 2003/0212379 A1 | 11/2003 | Bylund et al. |
| 2003/0216627 A1 | 11/2003 | Lorenz et al. |
| 2003/0220605 A1 | 11/2003 | Bowman, Jr. et al. |
| 2004/0010207 A1 | 1/2004 | Flaherty et al. |
| 2004/0034295 A1 | 2/2004 | Salganicoff |
| 2004/0045879 A1 | 3/2004 | Shults et al. |
| 2004/0051368 A1 | 3/2004 | Caputo et al. |
| 2004/0064259 A1 | 4/2004 | Haaland et al. |
| 2004/0097796 A1 | 5/2004 | Berman et al. |
| 2004/0116847 A1 | 6/2004 | Wall |
| 2004/0122353 A1 | 6/2004 | Shahmirian et al. |
| 2004/0133166 A1 | 7/2004 | Moberg et al. |
| 2004/0147034 A1 | 7/2004 | Gore et al. |
| 2004/0171983 A1 | 9/2004 | Sparks et al. |
| 2004/0203357 A1 | 10/2004 | Nassimi |
| 2004/0204868 A1 | 10/2004 | Maynard et al. |
| 2004/0215492 A1 | 10/2004 | Choi |
| 2004/0220517 A1 | 11/2004 | Starkweather et al. |
| 2004/0241736 A1 | 12/2004 | Hendee et al. |
| 2004/0249308 A1 | 12/2004 | Forssell |
| 2005/0003470 A1 | 1/2005 | Nelson et al. |
| 2005/0020980 A1 | 1/2005 | Inoue et al. |
| 2005/0022274 A1 | 1/2005 | Campbell et al. |
| 2005/0033148 A1 | 2/2005 | Haueter et al. |
| 2005/0049179 A1 | 3/2005 | Davidson et al. |
| 2005/0065464 A1 | 3/2005 | Talbot et al. |
| 2005/0065465 A1 | 3/2005 | Lebel et al. |
| 2005/0075624 A1 | 4/2005 | Miesel |
| 2005/0105095 A1 | 5/2005 | Pesach et al. |
| 2005/0137573 A1 | 6/2005 | McLaughlin |
| 2005/0171503 A1 | 8/2005 | Van Den Berghe et al. |
| 2005/0182306 A1 | 8/2005 | Sloan |
| 2005/0192494 A1 | 9/2005 | Ginsberg |
| 2005/0192557 A1 | 9/2005 | Brauker et al. |
| 2005/0197621 A1 | 9/2005 | Poulsen et al. |
| 2005/0203360 A1 | 9/2005 | Brauker et al. |
| 2005/0203461 A1 | 9/2005 | Flaherty et al. |
| 2005/0238507 A1 | 10/2005 | Dilanni et al. |
| 2005/0261660 A1 | 11/2005 | Choi |
| 2005/0272640 A1 | 12/2005 | Doyle, III et al. |
| 2005/0277912 A1 | 12/2005 | John |
| 2006/0009727 A1 | 1/2006 | OMahony et al. |
| 2006/0079809 A1 | 4/2006 | Goldberger et al. |
| 2006/0100494 A1 | 5/2006 | Kroll |
| 2006/0134323 A1 | 6/2006 | OBrien |
| 2006/0167350 A1 | 7/2006 | Monfre et al. |
| 2006/0173406 A1 | 8/2006 | Hayes et al. |
| 2006/0189925 A1 | 8/2006 | Gable et al. |
| 2006/0189926 A1 | 8/2006 | Hall et al. |
| 2006/0197015 A1 | 9/2006 | Sterling et al. |
| 2006/0200070 A1 | 9/2006 | Callicoat et al. |
| 2006/0204535 A1 | 9/2006 | Johnson |
| 2006/0229531 A1 | 10/2006 | Goldberger et al. |
| 2006/0253085 A1 | 11/2006 | Geismar et al. |
| 2006/0264895 A1 | 11/2006 | Flanders |
| 2006/0270983 A1 | 11/2006 | Lord et al. |
| 2006/0276771 A1 | 12/2006 | Galley et al. |
| 2006/0282290 A1 | 12/2006 | Flaherty et al. |
| 2007/0016127 A1 | 1/2007 | Staib et al. |
| 2007/0060796 A1 | 3/2007 | Kim |
| 2007/0060869 A1 | 3/2007 | Tolle et al. |
| 2007/0060872 A1 | 3/2007 | Hall et al. |
| 2007/0083160 A1 | 4/2007 | Hall et al. |
| 2007/0106135 A1 | 5/2007 | Sloan et al. |
| 2007/0116601 A1 | 5/2007 | Patton |
| 2007/0118405 A1 | 5/2007 | Campbell et al. |
| 2007/0129690 A1 | 6/2007 | Rosenblatt et al. |
| 2007/0142720 A1 | 6/2007 | Ridder et al. |
| 2007/0173761 A1 | 7/2007 | Kanderian et al. |
| 2007/0173974 A1 | 7/2007 | Lin |
| 2007/0179352 A1 | 8/2007 | Randlov et al. |
| 2007/0191716 A1 | 8/2007 | Goldberger et al. |
| 2007/0197163 A1 | 8/2007 | Robertson |
| 2007/0225675 A1 | 9/2007 | Robinson et al. |
| 2007/0244381 A1 | 10/2007 | Robinson et al. |
| 2007/0249007 A1 | 10/2007 | Rosero |
| 2007/0264707 A1 | 11/2007 | Liederman et al. |
| 2007/0282269 A1 | 12/2007 | Carter et al. |
| 2007/0287985 A1 | 12/2007 | Estes et al. |
| 2007/0293843 A1 | 12/2007 | Ireland et al. |
| 2008/0033272 A1 | 2/2008 | Gough et al. |
| 2008/0051764 A1 | 2/2008 | Dent et al. |
| 2008/0058625 A1 | 3/2008 | McGarraugh et al. |
| 2008/0065050 A1 | 3/2008 | Sparks et al. |
| 2008/0071157 A1 | 3/2008 | McGarraugh et al. |
| 2008/0071158 A1 | 3/2008 | McGarraugh et al. |
| 2008/0078400 A1 | 4/2008 | Martens et al. |
| 2008/0097289 A1 | 4/2008 | Steil et al. |
| 2008/0132880 A1 | 6/2008 | Buchman |
| 2008/0161664 A1 | 7/2008 | Mastrototaro et al. |
| 2008/0172026 A1 | 7/2008 | Blomquist |
| 2008/0177165 A1 | 7/2008 | Blomquist et al. |
| 2008/0188796 A1 | 8/2008 | Steil et al. |
| 2008/0200838 A1 | 8/2008 | Goldberger et al. |
| 2008/0206067 A1 | 8/2008 | De Corral et al. |
| 2008/0208113 A1 | 8/2008 | Damiano et al. |
| 2008/0214919 A1 | 9/2008 | Harmon et al. |
| 2008/0228056 A1 | 9/2008 | Blomquist et al. |
| 2008/0249386 A1 | 10/2008 | Besterman et al. |
| 2008/0269585 A1 | 10/2008 | Ginsberg |
| 2008/0269714 A1 | 10/2008 | Mastrototaro et al. |
| 2008/0269723 A1 | 10/2008 | Mastrototaro et al. |
| 2008/0287906 A1 | 11/2008 | Burkholz et al. |
| 2009/0006061 A1 | 1/2009 | Thukral et al. |
| 2009/0018406 A1 | 1/2009 | Yodat et al. |
| 2009/0030398 A1 | 1/2009 | Yodat et al. |
| 2009/0036753 A1 | 2/2009 | King |
| 2009/0043240 A1 | 2/2009 | Robinson et al. |
| 2009/0054753 A1 | 2/2009 | Robinson et al. |
| 2009/0069743 A1 | 3/2009 | Krishnamoorthy et al. |
| 2009/0069745 A1 | 3/2009 | Estes et al. |
| 2009/0069787 A1 | 3/2009 | Estes et al. |
| 2009/0099521 A1 | 4/2009 | Gravesen et al. |
| 2009/0105573 A1 | 4/2009 | Malecha |
| 2009/0131861 A1 | 5/2009 | Braig et al. |
| 2009/0156922 A1 | 6/2009 | Goldberger et al. |
| 2009/0156924 A1 | 6/2009 | Shariati et al. |
| 2009/0163781 A1 | 6/2009 | Say et al. |
| 2009/0198350 A1 | 8/2009 | Thiele |
| 2009/0221890 A1 | 9/2009 | Saffer et al. |
| 2009/0228214 A1 | 9/2009 | Say et al. |
| 2009/0318791 A1 | 12/2009 | Kaastrup |
| 2009/0326343 A1 | 12/2009 | Gable et al. |
| 2010/0057042 A1 | 3/2010 | Hayter |
| 2010/0114026 A1 | 5/2010 | Karratt et al. |
| 2010/0121170 A1 | 5/2010 | Rule |
| 2010/0137784 A1 | 6/2010 | Cefai et al. |
| 2010/0152658 A1 | 6/2010 | Hanson et al. |
| 2010/0174228 A1 | 7/2010 | Buckingham et al. |
| 2010/0211003 A1 | 8/2010 | Sundar et al. |
| 2010/0228110 A1 | 9/2010 | Tsoukalis |
| 2010/0262117 A1 | 10/2010 | Magni et al. |
| 2010/0262434 A1 | 10/2010 | Shaya |
| 2010/0295686 A1 | 11/2010 | Sloan et al. |
| 2010/0298765 A1 | 11/2010 | Budiman et al. |
| 2011/0021584 A1 | 1/2011 | Berggren et al. |
| 2011/0028817 A1 | 2/2011 | Jin et al. |

(56) References Cited

U.S. PATENT DOCUMENTS

| | | |
|---|---|---|
| 2011/0054390 A1 | 3/2011 | Searle et al. |
| 2011/0054399 A1 | 3/2011 | Chong et al. |
| 2011/0124996 A1 | 5/2011 | Reinke et al. |
| 2011/0144586 A1 | 6/2011 | Michaud et al. |
| 2011/0145747 A1* | 6/2011 | Wong .................... G16H 10/20 709/219 |
| 2011/0160652 A1 | 6/2011 | Yodat et al. |
| 2011/0178472 A1 | 7/2011 | Cabiri |
| 2011/0190694 A1 | 8/2011 | Lanier, Jr. et al. |
| 2011/0202005 A1 | 8/2011 | Yodat et al. |
| 2011/0208155 A1* | 8/2011 | Palerm .................. G16H 40/60 604/503 |
| 2011/0218495 A1 | 9/2011 | Remde |
| 2011/0230833 A1 | 9/2011 | Landman et al. |
| 2011/0251509 A1 | 10/2011 | Beyhan et al. |
| 2011/0257496 A1* | 10/2011 | Terashima ............... A61B 5/74 600/347 |
| 2011/0313680 A1 | 12/2011 | Doyle et al. |
| 2011/0316562 A1 | 12/2011 | Cefai et al. |
| 2012/0003935 A1 | 1/2012 | Lydon et al. |
| 2012/0010594 A1 | 1/2012 | Holt et al. |
| 2012/0030393 A1 | 2/2012 | Ganesh et al. |
| 2012/0053556 A1 | 3/2012 | Lee |
| 2012/0078067 A1 | 3/2012 | Kovatchev et al. |
| 2012/0078161 A1 | 3/2012 | Masterson et al. |
| 2012/0078181 A1 | 3/2012 | Smith et al. |
| 2012/0101451 A1 | 4/2012 | Boit et al. |
| 2012/0123234 A1 | 5/2012 | Atlas et al. |
| 2012/0136336 A1 | 5/2012 | Mastrototaro et al. |
| 2012/0190955 A1 | 7/2012 | Rao et al. |
| 2012/0203085 A1 | 8/2012 | Rebec |
| 2012/0203178 A1 | 8/2012 | Tverskoy |
| 2012/0215087 A1 | 8/2012 | Cobelli et al. |
| 2012/0225134 A1 | 9/2012 | Komorowski |
| 2012/0226259 A1 | 9/2012 | Yodat et al. |
| 2012/0232520 A1 | 9/2012 | Sloan et al. |
| 2012/0238851 A1 | 9/2012 | Kamen et al. |
| 2012/0271655 A1 | 10/2012 | Knobel et al. |
| 2012/0277668 A1 | 11/2012 | Chawla |
| 2012/0282111 A1 | 11/2012 | Nip et al. |
| 2012/0295550 A1 | 11/2012 | Wilson et al. |
| 2013/0030358 A1 | 1/2013 | Yodfat et al. |
| 2013/0158503 A1 | 6/2013 | Kanderian, Jr. et al. |
| 2013/0178791 A1 | 7/2013 | Javitt |
| 2013/0231642 A1 | 9/2013 | Doyle et al. |
| 2013/0253472 A1 | 9/2013 | Cabiri |
| 2013/0261406 A1 | 10/2013 | Rebec et al. |
| 2013/0296823 A1 | 11/2013 | Melker et al. |
| 2013/0317753 A1 | 11/2013 | Kamen et al. |
| 2013/0338576 A1 | 12/2013 | OConnor et al. |
| 2014/0005633 A1 | 1/2014 | Finan |
| 2014/0066886 A1 | 3/2014 | Roy et al. |
| 2014/0074033 A1 | 3/2014 | Sonderegger et al. |
| 2014/0121635 A1 | 5/2014 | Hayter |
| 2014/0128839 A1 | 5/2014 | Dilanni et al. |
| 2014/0135880 A1 | 5/2014 | Baumgartner et al. |
| 2014/0146202 A1 | 5/2014 | Boss et al. |
| 2014/0180203 A1 | 6/2014 | Budiman et al. |
| 2014/0180240 A1 | 6/2014 | Finan et al. |
| 2014/0200426 A1 | 7/2014 | Taub et al. |
| 2014/0200559 A1 | 7/2014 | Doyle et al. |
| 2014/0230021 A1 | 8/2014 | Birtwhistle et al. |
| 2014/0276554 A1 | 9/2014 | Finan et al. |
| 2014/0276556 A1 | 9/2014 | Saint et al. |
| 2014/0278123 A1 | 9/2014 | Prodhom et al. |
| 2014/0309615 A1 | 10/2014 | Mazlish |
| 2014/0316379 A1 | 10/2014 | Sonderegger et al. |
| 2014/0325065 A1 | 10/2014 | Birtwhistle et al. |
| 2015/0018633 A1 | 1/2015 | Kovachev et al. |
| 2015/0025329 A1 | 1/2015 | Amarasingham et al. |
| 2015/0025495 A1 | 1/2015 | Peyser |
| 2015/0120317 A1 | 4/2015 | Mayou et al. |
| 2015/0134265 A1 | 5/2015 | Kohlbrecher et al. |
| 2015/0165119 A1 | 6/2015 | Palerm et al. |
| 2015/0173674 A1 | 6/2015 | Hayes et al. |
| 2015/0213217 A1 | 7/2015 | Amarasingham et al. |
| 2015/0217052 A1 | 8/2015 | Keenan et al. |
| 2015/0217053 A1 | 8/2015 | Booth et al. |
| 2015/0265767 A1 | 9/2015 | Vazquez et al. |
| 2015/0306314 A1 | 10/2015 | Doyle et al. |
| 2015/0351671 A1 | 12/2015 | Vanslyke et al. |
| 2015/0366945 A1 | 12/2015 | Greene |
| 2016/0015891 A1 | 1/2016 | Papiorek |
| 2016/0038673 A1 | 2/2016 | Morales |
| 2016/0038689 A1 | 2/2016 | Lee et al. |
| 2016/0051749 A1 | 2/2016 | Istoc |
| 2016/0082187 A1 | 3/2016 | Schaible et al. |
| 2016/0089494 A1 | 3/2016 | Guerrini |
| 2016/0175520 A1 | 6/2016 | Palerm et al. |
| 2016/0228641 A1 | 8/2016 | Gescheit et al. |
| 2016/0243318 A1 | 8/2016 | Despa et al. |
| 2016/0256087 A1 | 9/2016 | Doyle et al. |
| 2016/0287512 A1 | 10/2016 | Cooper et al. |
| 2016/0302054 A1 | 10/2016 | Kimura et al. |
| 2016/0331310 A1 | 11/2016 | Kovatchev |
| 2016/0354543 A1 | 12/2016 | Cinar et al. |
| 2017/0049386 A1 | 2/2017 | Abraham et al. |
| 2017/0143899 A1 | 5/2017 | Gondhalekar et al. |
| 2017/0143900 A1 | 5/2017 | Rioux et al. |
| 2017/0156682 A1 | 6/2017 | Doyle et al. |
| 2017/0173261 A1 | 6/2017 | OConnor et al. |
| 2017/0189625 A1 | 7/2017 | Cirillo et al. |
| 2017/0281877 A1 | 10/2017 | Marlin et al. |
| 2017/0296746 A1 | 10/2017 | Chen et al. |
| 2017/0311903 A1 | 11/2017 | Davis et al. |
| 2017/0348482 A1 | 12/2017 | Duke et al. |
| 2018/0036495 A1 | 2/2018 | Searle et al. |
| 2018/0040255 A1 | 2/2018 | Freeman et al. |
| 2018/0075200 A1 | 3/2018 | Davis et al. |
| 2018/0075201 A1 | 3/2018 | Davis et al. |
| 2018/0075202 A1 | 3/2018 | Davis et al. |
| 2018/0092576 A1 | 4/2018 | Ambrosio |
| 2018/0126073 A1 | 5/2018 | Wu et al. |
| 2018/0169334 A1 | 6/2018 | Grosman et al. |
| 2018/0200434 A1 | 7/2018 | Mazlish et al. |
| 2018/0200438 A1 | 7/2018 | Mazlish et al. |
| 2018/0200441 A1 | 7/2018 | Desborough et al. |
| 2018/0204636 A1 | 7/2018 | Edwards et al. |
| 2018/0277253 A1 | 9/2018 | Gondhalekar et al. |
| 2018/0289891 A1 | 10/2018 | Finan et al. |
| 2018/0296757 A1 | 10/2018 | Finan et al. |
| 2018/0342317 A1 | 11/2018 | Skirble et al. |
| 2018/0369479 A1 | 12/2018 | Hayter et al. |
| 2019/0076600 A1 | 3/2019 | Grosman et al. |
| 2019/0240403 A1 | 8/2019 | Palerm et al. |
| 2019/0290844 A1 | 9/2019 | Monirabbasi et al. |
| 2019/0336683 A1 | 11/2019 | O'Connor et al. |
| 2019/0336684 A1 | 11/2019 | OConnor et al. |
| 2019/0348157 A1 | 11/2019 | Booth et al. |
| 2020/0046268 A1 | 2/2020 | Patek et al. |
| 2020/0101222 A1 | 4/2020 | Lintereur et al. |
| 2020/0101223 A1 | 4/2020 | Lintereur et al. |
| 2020/0101225 A1 | 4/2020 | OConnor et al. |
| 2020/0219625 A1 | 7/2020 | Kahlbaugh |
| 2020/0342974 A1 | 10/2020 | Chen et al. |
| 2021/0050085 A1 | 2/2021 | Hayter et al. |
| 2021/0098105 A1 | 4/2021 | Lee et al. |
| 2022/0023536 A1 | 1/2022 | Graham et al. |

FOREIGN PATENT DOCUMENTS

| | | |
|---|---|---|
| CN | 1297140 A | 5/2001 |
| DE | 19756872 A1 | 7/1999 |
| EP | 0341049 A2 | 11/1989 |
| EP | 0496305 A2 | 7/1992 |
| EP | 0549341 A1 | 6/1993 |
| EP | 1491144 A1 | 12/2004 |
| EP | 1571582 A2 | 9/2005 |
| EP | 0801578 B1 | 7/2006 |
| EP | 2666520 A1 | 10/2009 |
| EP | 2139382 A1 | 1/2010 |
| EP | 2397181 A1 | 12/2011 |
| EP | 2695573 A2 | 2/2014 |
| EP | 2830499 A1 | 2/2015 |

(56) References Cited

FOREIGN PATENT DOCUMENTS

| | | |
|---|---|---|
| EP | 2943149 A1 | 11/2015 |
| EP | 3177344 A1 | 6/2017 |
| EP | 3314548 A1 | 5/2018 |
| EP | 2897071 B1 | 5/2019 |
| EP | 3607985 A1 | 2/2020 |
| GB | 2443261 A | 4/2008 |
| JP | 51125993 A | 11/1976 |
| JP | 02131777 A | 5/1990 |
| JP | 2004283378 A | 10/2004 |
| JP | 2017525451 A | 9/2017 |
| JP | 2018153569 A | 10/2018 |
| JP | 2019525276 A | 9/2019 |
| TW | 200740148 A | 10/2007 |
| TW | M452390 U | 5/2013 |
| WO | 9800193 A1 | 1/1998 |
| WO | 9956803 A1 | 11/1999 |
| WO | 0030705 A1 | 6/2000 |
| WO | 0032258 A1 | 6/2000 |
| WO | 0172354 A2 | 10/2001 |
| WO | 2002015954 A1 | 2/2002 |
| WO | 0243866 A2 | 6/2002 |
| WO | 02082990 A1 | 10/2002 |
| WO | 03016882 A1 | 2/2003 |
| WO | 03039362 A1 | 5/2003 |
| WO | 03045233 A1 | 6/2003 |
| WO | 2004043250 A1 | 5/2004 |
| WO | 04092715 A1 | 10/2004 |
| WO | 2005051170 A2 | 6/2005 |
| WO | 2005082436 A1 | 9/2005 |
| WO | 05110601 A1 | 11/2005 |
| WO | 2005113036 A1 | 12/2005 |
| WO | 2006053007 A2 | 5/2006 |
| WO | 2007064835 A2 | 6/2007 |
| WO | 2007078937 A1 | 7/2007 |
| WO | 2008024810 A2 | 2/2008 |
| WO | 2008029403 A1 | 3/2008 |
| WO | 2008133702 A1 | 11/2008 |
| WO | 2009045462 A1 | 4/2009 |
| WO | 2009049252 A1 | 4/2009 |
| WO | 2009066287 A3 | 5/2009 |
| WO | 2009066288 A1 | 5/2009 |
| WO | 2009098648 A2 | 8/2009 |
| WO | 2009134380 A2 | 11/2009 |
| WO | 2010053702 A1 | 5/2010 |
| WO | 2010132077 A1 | 11/2010 |
| WO | 2010138848 A1 | 12/2010 |
| WO | 2010147659 A2 | 12/2010 |
| WO | 2011095483 A1 | 8/2011 |
| WO | 2012045667 A2 | 4/2012 |
| WO | 2012108959 A1 | 8/2012 |
| WO | 2012134588 A1 | 10/2012 |
| WO | 2012177353 A1 | 12/2012 |
| WO | 2012178134 A2 | 12/2012 |
| WO | 2013078200 A1 | 5/2013 |
| WO | 2013134486 A2 | 9/2013 |
| WO | 20130149186 A1 | 10/2013 |
| WO | 2013177565 A1 | 11/2013 |
| WO | 2013182321 A1 | 12/2013 |
| WO | 2014109898 A1 | 7/2014 |
| WO | 2014110538 A1 | 7/2014 |
| WO | 2014194183 A2 | 12/2014 |
| WO | 2015056259 A1 | 4/2015 |
| WO | 2015061493 A1 | 4/2015 |
| WO | 2015073211 A1 | 5/2015 |
| WO | 2015081337 A2 | 6/2015 |
| WO | 2015187366 A1 | 12/2015 |
| WO | 2016004088 A1 | 1/2016 |
| WO | 2016022650 A1 | 2/2016 |
| WO | 2016041873 A1 | 3/2016 |
| WO | 2016089702 A1 | 6/2016 |
| WO | 2016141082 A1 | 9/2016 |
| WO | 2016161254 A1 | 10/2016 |
| WO | 2017004278 A1 | 1/2017 |
| WO | 2017091624 A1 | 6/2017 |
| WO | 2017105600 A1 | 6/2017 |
| WO | 2017184988 A1 | 10/2017 |
| WO | 2017205816 A1 | 11/2017 |
| WO | 2018009614 A1 | 1/2018 |
| WO | 2018067748 A1 | 4/2018 |
| WO | 2018120104 A1 | 7/2018 |
| WO | 2018136799 A1 | 7/2018 |
| WO | 2018204568 A1 | 11/2018 |
| WO | 2019077482 A1 | 4/2019 |
| WO | 2019094440 A1 | 5/2019 |
| WO | 2019213493 A1 | 11/2019 |
| WO | 2019246381 A1 | 12/2019 |
| WO | 2020081393 A1 | 4/2020 |
| WO | 2021011738 A1 | 1/2021 |

OTHER PUBLICATIONS

Montaser Eslam et al., "Seasonal Local Models for Glucose Prediction in Type 1 Diabetes", IEE Journal of Biomedical and Health Informatics, IEEE, Piscataway, NJ, USA, vol. 24, No. 7, Nov. 29, 2019, pp. 2064-2072.

Samadi Sediqeh et al., "Automatic Detection and Estimation of Unannouced Meals for Multivariable Artificial Pancreas System", Diabetis Technology & Therapeutics, vol. 20m No. 3, Mar. 1, 2018, pp. 235-246.

Samadi Sediqeh et al., "Meal Detection and Carbohydrate Estimation Using Continuous Glucose Sensor Data" IEEE Journal of Biomedical and Health Informatics, IEEE, Piscataway, NJ, USA, vol. 21, No. 3, May 1, 2017, pp. 619-627.

Khodaei et al., "Physiological Closed-Loop Contol (PCLC) Systems: Review of a Modern Frontier in Automation", IEEE Access, IEEE, USA, vol. 8, Jan. 20, 2020, pp. 23965-24005.

E. Atlas et al., "MD-Logic Artificial Pancreas System: A pilot study in adults with type 1 diabetes", Diabetes Care, vol. 33, No. 5, Feb. 11, 2010, pp. 1071-1076.

Anonymous: "Fuzzy control system", Wikipedia, Jan. 10, 2020. URL: https://en.wikipedia.org/w/index.php?title=Fuzzy_control_system&oldid=935091190 Retrieved: May 25, 2021.

International Search Report and Written Opinion for the International Patent Application No. PCT/US2021/016283, dated Jun. 2, 2021, 15 pages.

International Search Report and Written Opinion for the International Patent Application No. PCT/US2021/022694, dated Jun. 25, 2021, 13 pages.

European Search Report for the European Patent Application No. 21168591.2, dated Oct. 13, 2021, 4 pages.

International Search Report and Written Opinion for the International Patent Application No. PCT/US2021/041954, dated Oct. 25, 2021, 13 pages.

International Search Report and Written Opinion for the International Patent Application No. PCT/US2021/047771, dated Dec. 22, 2021, 11 pages.

International Search Report and Written Opinion for the International Patent Application No. PCT/US2021/052855, dated Dec. 22, 2021, 11 pages.

Anonymous: "Artificial pancreas—Wikipedia", Mar. 13, 2018 (Mar. 13, 2018), XP055603712, Retrieved from the Internet: URL: https://en.wikipedia.org/wiki/Artificial_pancreas [retrieved on Jul. 9, 2019] section "Medical Equipment" and the figure labeled "The medical equipment approach to an artifical pancreas".

Kaveh et al., "Blood Glucose Regulation via Double Loop Higher Order Sliding Mode Control and Multiple Sampling Rate." Paper presented at the proceedings of the 17th IFAC World Congress, Seoul, Korea (Jul. 2008).

Dassau et al., "Real-Time Hypoglycemia Prediction Suite Using Contineous Glucose Monitoring," Diabetes Care, vol. 33, No. 6, 1249-1254 (2010).

International Search Report and Written Opinion for International Patent Application No. PCT/US17/53262, dated Dec. 13, 2017, 8 pages.

Van Heusden et al., "Control-Relevant Models for Glucose Control using a Priori Patient Characteristics", IEEE Transactions on Biomedical Engineering, vol. 59, No. 7, (Jul. 1, 2012) pp. 1839-1849.

(56) References Cited

OTHER PUBLICATIONS

Doyle III et al., "Run-to-Run Control Strategy for Diabetes Management." Paper presented at 23rd Annual International Conference of the IEEE Engineering in Medicine and Biology Society, Istanbul, Turkey (Oct. 2001).
Bequette, B.W., and Desemone, J., "Intelligent Dosing Systems": Need for Design and Analysis Based on Control Theory, Diabetes Technology and Therapeutics 9(6): 868-873 (2004).
Parker et al., "A Model-Based Agorithm for Blood Gucose Control in Type 1 Diabetic Patients." IEEE Transactions on Biomedical Engineering, 46 (2) 148-147 (1999).
International Search Report and Written Opinion for International Patent Application No. PCT/US2017/015601, dated May 16, 2017, 12 pages.
International Search Report and Written Opinion for the International Patent Application No. PCT/US2018/018901, dated Aug. 6, 2018, 12 pages.
International Search Report and Written Opinion for International Patent Application No. PCT/US2018/052467, dated Jan. 4, 2019, 13 pages.
"How to Create a QR Code that Deep Links to Your Mobile App", Pure Oxygen Labs, web<https://pureoxygenlabs.com/how-to-create-a-qr-codes-that-deep-link-to-your-mobile-app/>. Year:2017.
"Read NFC Tags with an iPHone App on iOS 11", GoToTags, Sep. 11, 2017, web <https://gototags.com/blog/read-nfc-tags-with-an-iphone-app-on-ios-11/>. (Year:2017).
International Search Report and Written Opinion for International Patent Application No. PCT/US2016/063350, dated Mar. 27, 2017, 9 pages.
Extended Search Report dated Aug. 13, 2018, issued in European Patent Application No. 16753053.4, 9 pages.
International Search Report and Written Opinion for International Patent Application No. PCT/US16/18452, dated Apr. 29, 2015, 9 pages.
International Preliminary Report on Patentability dated Aug. 31, 2017, issued in PCT Patent Application No. PCT/US2016/018452, 7 pages.
International Search Report and Written Opinion for International Patent Application No. PCT/US2019/055862, dated Mar. 11, 2020.
Unger, Jeff, et al., "Glucose Control in the Hospitalized Patient," Emerg. Med 36(9):12-18 (2004).
Glucommander FAQ downloaded from https://adaendo.com/GlucommanderFAQ.html on Mar. 16, 2009.
Finfer, Simon & Heritier, Stephane. (2009). The NICE-SUGAR (Normoglycaemia in Intensive Care Evaluation and Survival Using Glucose Algorithm Regulation) Study: statistical analysis plan. Critical care and resuscitation : journal of the Australasian Academy of Critical Care Medicine. 11. 46-57.
Letters to the Editor regarding "Glucose Control in Critically Ill Patients," N Engl J Med 361: 1, Jul. 2, 2009.
"Medtronic is Leading a Highly Attractive Growth Market," Jun. 2, 2009.
Davidson, Paul C., et al. "Glucommander: An Adaptive, Computer-Directed System for IV Insulin Shown to be Safe, Simple, and Effective in 120,618 Hours of Operation," Atlanta Diabetes Associates presentation Nov. 16, 2003.
Davidson, Paul C., et al. "Pumpmaster and Glucommander," presented at the MiniMed Symposium, Atlanta GA, Dec. 13, 2003.
Kanji S., et al. "Reliability of point-of-care testing for glucose measurement in critically ill adults," Critical Care Med, vol. 33, No. 12, pp. 2778-2785, 2005.
Krinsley James S., "Severe hypoglycemia in critically ill patients: Risk factors and outcomes," Critical Care Med, vol. 35, No. 10, pp. 1-6, 2007.
International Searching Authority, Invitation to Pay Additional Fees, International Application No. PCT/US2006/004929, dated Jul. 27, 2006.
Farkas et al. ""Single-Versus Triple-Lumen Central Catheter-Related Sepsis: A Prospective Randomized Study in a Critically Ill Population"" The American Journal of Medicine Sep. 1992 vol. 93 p. 277-282.
Davidson, Paul C., et al., A computer-directed intravenous insulin system shown to be safe, simple,and effective in 120,618 h of operation, Diabetes Care, vol. 28, No. 10, Oct. 2005, pp. 2418-2423.
Gorke, A. "Microbial contamination of haemodialysis catheter connections." EDTNA/ERCA journal (English ed.) vol. 31,2 (2005): 79-84. doi:10.1111/j.1755-6686.2005.tb00399.x.
Lovich et al. "Central venous catheter infusions: A laboratory model shows large differences in drug delivery dynamics related to catheter dead volume" Critical Care Med 2007 vol. 35, No. 12.
Van Den Berghe, Greet, M.D., Ph.D., et al., Intensive Insulin Therapy in Critically Ill Patients, The New England Journal of Medicine, vol. 345, No. 19, Nov. 8, 2001, pp. 1359-1367.
Templeton et al, "Multilumen Central Venous Catheters Increase Risk for Catheter-Related Bloodstream Infection Prospective Surveillance Study" Infection 2008; 36: 322-327.
Wilson, George S., et al., Progress toward the Development of an Implantable Sensor for Glucose, Clin. Chem., vol. 38, No. 9, 1992, pp. 1613-1617.
Yeung et al. "Infection Rate for Single Lumen v Triple Lumen Subclavian Catheters" Infection Control and Hospital Epidemiology, vol. 9, No. 4 (Apr. 1988) pp. 154-158 The University of Chicago Press.
International Search Report and Written Opinion, International Application No. PCT/US2010/033794 dated Jul. 16, 2010.
International Search Report and Written Opinion in PCT/US2008/079641 dated Feb. 25, 2009.
Berger, ""Measurement of Analytes in Human Serum and Whole Blood Samples by Near-Infrared Raman Spectroscopy,"" Ph.D. Thesis, Massachusetts Institute of Technology, Chapter 4, pp. 50-73, 1998.
Berger, "An Enhanced Algorithm for Linear Multivariate Calibration," Analytical Chemistry, vol. 70, No. 3, pp. 623-627, Feb. 1, 1998.
Billman et al.,"Clinical Performance of an In line Ex-Vivo Point of Care Monitor: A Multicenter Study," Clinical Chemistry 48: 11, pp. 2030-2043, 2002.
Widness et al., "Clinical Performance on an In-Line Point-of-Care Monitor in Neonates"; Pediatrics, vol. 106, No. 3, pp. 497-504, Sep. 2000.
Finkielman et al., "Agreement Between Bedside Blood and Plasma Glucose Measurement in the ICU Setting"; retrieved from http://www.chestjournal.org; CHEST/127/5/May 2005.
Glucon Critical Care Blood Glucose Monitor; Glucon; retrieved from http://www.glucon.com.
Fogt, et al., "Development and Evaluation of a Glucose Analyzer for a Glucose-Controlled Insulin Infusion System (Biostator)"; Clinical Chemistry, vol. 24, No. 8, pp. 1366-1372, 1978.
Vonach et al., "Application of Mid-Infrared Transmission Spectrometry to the Direct Determination of Glucose in Whole Blood," Applied Spectroscopy, vol. 52, No. 6, 1998, pp. 820-822.
Muniyappa et al., "Current Approaches for assessing insulin sensitivity and resistance in vivo: advantages, limitations, and appropriate usage," AJP—ndocrinol Metab, vol. 294, E15-E26, first published Oct. 23, 2007.
R Anthony Shaw, et al., "Infrared Spectroscopy in Clinical and Dianostic Analysis," Encyclopedia of Analytical Chemistry, ed. Robert A. Meyers, John Wiley & Sons, Ltd., pp. 1-20, 2000.
International Preliminary Report on Patentability for the International Patent Application No. PCT/US2019/053603, dated Apr. 8, 2021, 9 pages.
International Search Report and Written Opinion for the International Patent Application No. PCT/US2019/053603, dated Jan. 7, 2020, 16 pages.
Dassau et al., "Detection of a meal using continuous glucose monitoring: Implications for an artificial [beta]-cell." Diabetes Care, American Diabetes Association, Alexandria, VA, US, 31(2):295-300 (2008).

(56) References Cited

OTHER PUBLICATIONS

Cameron et al., "Probabilistic Evolving Meal Detection and Estimation of Meal Total Glucose Appearance Author Affiliations", J Diabetes Sci and Tech,vol., Diabetes Technology Society ;(5):1022-1030 (2009).

Lee et al., "A closed-loop artificial pancreas based on model predictive control: Human-friendly identification and automatic meal disturbance rejection", Biomedical Signal Processing and Control, Elsevier, Amsterdam, NL, 4(4):1746-8094 (2009).

International Search Report and Written Opinion for the InternationalPatent Application No. PCT/US2021/018297, mailed May 18, 2021, 18 pages.

An Emilia Fushimi: "Artificial Pancreas: Evaluating the ARG Algorithm Without Meal Annoucement", Journal of Diabetes Science and Technology Diabetes Technology Society, Mar. 22, 2019, pp. 1025-1043.

International Search Report and Written Opinion for the InternationalPatent Application No. PCT/US2021/017441, dated May 25, 2021, 12 pages.

International Search Report and Written Opinion for the InternationalPatent Application No. PCT/US2021/017664, dated May 26, 2021, 16 pages.

Mirko Messori et al: "Individualized model predictive control for the artificial pancreas: In silico evaluation of closed-loop glucose control", IEEE Control Systems, vol. 38, No. 1, Feb. 1, 2018, pp. 86-104.

International Search Report and Written Opinion for the International Patent Application No. PCT/US2021/017662, dated May 26, 2021, 14 pages.

Anonymous: "Reservoir Best Practice and Top Tips" Feb. 7, 2016, URL: https://www.medtronic-diabetes.co.uk/blog/reservoir-best-practice-and-top-tips, p. 1.

Gildon Bradford: "InPen Smart Insulin Pen System: Product Review and User Experience" Diabetes Spectrum, vol. 31, No. 4, Nov. 15, 2018, pp. 354-358.

International Search Report and Written Opinion for the International Patent Application No. PCT/US2021/016050, dated May 27, 2021, 16 pages.

International Search Report and Written Opinion for the International Patent Application No. PCT/US2020/065226, dated May 31, 2021, 18 pages.

International Search Report and Written Opinion for the International Patent Application No. PCT/US2021/017659, dated May 31, 2021, 13 pages.

Anonymous: "Fuzzy control system", Wikipedia, Jan. 10, 2020. URL: https://en.wikipedia.org/w/index.php?title=Fuzzy_control_system&oldid=935091190

International Search Report and Written Opinion for International Patent Application No. PCT/US2021/051027, dated Jan. 7, 2022, 16 pages.

International Search Report and Written Opinion for International Patent Application No. PCT/US2021/052372, dated Jan. 26, 2022, 15 pages.

International Search Report and Written Opinion for the International Patent Application No. PCT/US2021/046607, dated Jan. 31, 2022, 20 pages.

International Search Report and Written Opinion for the International Patent Application No. PCT/US2021/055745, dated Feb. 14, 2022, 13 pages.

International Search Report and Written Opinion for the International Patent Application No. PCT/US2020/052125, dated Aug. 12, 2020, 15 pages.

International Search Report and Written Opinion for the International Patent Application No. PCT/US2020/050332, dated Sep. 12, 2020, 12 pages.

European Patent Office, "Notification of Transmittal of the ISR and the Written Opinion of the International Searching Authority, or the Declaration," in PCT Application No. PCT/GB2015/050248, dated Jun. 23, 2015, 12 pages.

International Search Report and Written Opinion for the International Patent Application No. PCT/US2022/013470, dated May 6, 2022, 14 pages.

International Search Report and Written Opinion for the International Patent Application No. PCT/US2022/013473, dated May 6, 2022, 13 pages.

International Search Report and Written Opinion for the International Patent Application No. PCT/US2022/019079, dated Jun. 2, 2022, 14 pages.

International Search Report and Written Opinion for the International Patent Application No. PCT/US2022/018453, dated Jun. 2, 2022, 13 pages.

International Search Report and Written Opinion for the International Patent Application No. PCT/US22/018700, dated Jun. 7, 2022, 13 pages.

International Search Report and Written Opinion for the International Patent Application No. PCT/US22/019080, dated Jun. 7, 2022, 14 pages.

International Search Report and Written Opinion for the International Patent Application No. PCT/US22/019664, dated Jun. 7, 2022, 14 pages.

International Search Report and Written Opinion for the International Patent Application No. PCT/US21/060618, dated Mar. 21, 2022, 15 pages.

Herrero Pau et al: "Enhancing automatic closed-loop glucose control in type 1 diabetes with an adaptive meal polus calculator-in silicoevaluation under intra-day variability", Computer Methods and Programs in Biomedicine, Elsevier, Amsterdam, NL, vol. 146, Jun. 1, 2017 (Jun. 1, 2017), pp. 125-131, XP085115607, ISSN: 0169-2607, D0I:10.1016/J.CMPB.2017.05.010.

Marie Aude Qemerais: "Preliminary Evaluation of a New Semi-Closed-Loop Insulin Therapy System over the prandial period in Adult Patients with type I diabetes: the WP6. 0 Diabeloop Study", Journal of Diabetes Science and Technology Diabetes Technology Society Reprintsand permissions, Jan. 1, 2014, pp. 1177-1184, Retrieved from the Internet: URL:http://journals.sagepub.com/doi/pdf/10.1177/1932296814545668 [retrieved on Jun. 6, 2022] chapter "Functioning of the Algorithm" chapter "Statistical Analysis" p. 1183, left-hand column, line 16- line 23.

Anonymous: "Kernel density estimation", Wikipedia, Nov. 13, 2020 (Nov. 13, 2020), pp. 1-12, XP055895569, Retrieved from the Internet: URL:https://en.wikipedia.org/w/index.php?title=Kemnel_density_estimation&oldid=988508333 [retrieved on Jun. 6, 2022].

Anonymous: "openaps / oref0 /lib/determine-basal-js", openaps repository, Nov. 9, 2019 (Nov. 9, 2019), pp. 1-17, XP055900283, Retrieved from the Internet: URL:https://github.com/openaps/oref0/blob/master/lib/determine-basal/determine-basal.js [retrieved on Jun. 6, 2022] line 116-line 118, line 439-line 446.

Anonymous: "AndroidAPS screens", AndroidAPS documentation, Oct. 4, 2020 (Oct. 4, 2020), pp. 1-12, XP055894824, Retrieved from the Internet: URL:https://github.com/openaps/AndroidAPSdocs/blob/25d8acf8b28262b411b34f416f173ac0814d7e14/docs/EN/Getting-Started/Screenshots.md [retrieved on Jun. 6, 2022].

Kozak Milos et al: "Issue #2473 of AndroidAPS", MilosKozak / AndroidAPS Public repository, Mar. 4, 2020 (Mar. 4, 2020), pp. 1-4, XP055900328, Retrieved from the Internet: URL:https://github.com/MilosKozak/AndroidAPS/isues/2473 [retrieved on Jun. 6, 2022].

Medication Bar Code System Implementation Planning Section I: A Bar Code Primer for Leaders, Aug. 2013.

Medication Bar Code System Implementation Planning Section II: Building the Case for Automated Identification of Medications, Aug. 2013.

Villareal et al. (2009) in: Distr. Comp. Art. Intell. Bioninf. Soft Comp. Amb. Ass. Living; Int. Work Conf. Art. Neural Networks (IWANN) 2009, Leet. Notes Comp. Sci vol. 5518; S. Omatu et al. (Eds.), pp. 870-877.

Fox, Ian G.; Machine Learning for Physiological Time Series: Representing and Controlling Blood Glucose for Diabetes Management; University of Michigan. ProQuest Dissertations Publishing, 2020. 28240142. (Year: 2020).

(56) References Cited

OTHER PUBLICATIONS

International Search Report and Written Opinion for the International Patent Application No. PCT/US2022/012896, dated Apr. 22, 2022, 15 pages.

* cited by examiner

ACTIVITY MODE FOR ARTIFICIAL PANCREAS SYSTEM

CROSS-REFERENCE TO RELATED APPLICATIONS

This application claims priority to U.S. Provisional Application No. 62/738,531, filed on Sep. 28, 2018, the entire contents of which are incorporated herein by reference.

TECHNICAL FIELD

The disclosed examples generally relate to medication delivery. More particularly, the disclosed examples relate to techniques, processes, devices or systems for managing operation of a wearable drug delivery device based on detected activity levels of a user, detected locations of the user, or learned behavior of the user.

BACKGROUND

Many conventional wearable drug delivery devices may include settings that allow for temporary adjustments to regular insulin delivery. The setting may include a setting that permits the suspension of delivery of insulin. These conventional drug delivery devices, however, may not enable adjusting the delivery of insulin, either automatically or through manual instruction, based on increased activity levels of the user or detected periods of increased insulin requirements.

Accordingly, there is a need for a wearable drug delivery device that may adjust insulin delivery based on manual request or automatically during detected increases in or expected increased activity levels of the user or based on detected locations of the user where adjustments to delivery were previously implemented.

SUMMARY

Disclosed is a wearable drug delivery device. The disclosed wearable drug delivery device is operable to deliver insulin to a user. The wearable drug delivery device includes a reservoir, a pump mechanism, an inertial measurement unit, and a controller. The reservoir configured to store insulin. The pump mechanism is coupled to the reservoir and operable to expel the stored insulin from the reservoir. The inertial measurement unit is operable to detect an activity level of the user. The controller is communicatively coupled to the pump mechanism and the inertial measurement unit. The controller, when in an activity mode of operation, is operable to receive an input from the inertial measurement unit, wherein the input indicates one or more measurements of motion. The controller may determine, from the received input, an activity level change. Based on the determined activity level change, the controller may modify an amount of insulin to be delivered by the pump mechanism. The controller may output a signal to the pump mechanism actuating delivery of the modified amount of insulin.

Disclosed is a non-transitory computer readable medium embodied with programming code executable by a processor, and the processor when executing the programming code is operable to perform functions. The functions performed by the processor include receiving inputs associated with an activity mode. The processor may evaluate the received inputs with reference to activity mode thresholds and determine whether the evaluated inputs exceed the activity mode thresholds. In response to the evaluated inputs exceeding the activity mode thresholds, the processor initiates the activity mode. Based on initiation of the activity mode, the processor may adjust parameters of a diabetes treatment plan. The processor may actuate delivery of insulin via a pump mechanism according to the adjusted parameters of the diabetes treatment plan.

DETAILED DESCRIPTION

This disclosure presents various systems, components, and methods operable to adjust insulin delivery to a user based on an available activity mode of operation of a drug delivery device worn by the user. Each of the systems, components, and methods disclosed herein provides one or more advantages over conventional systems, components, and methods.

An example provides a process that may be used with any additional algorithms or computer applications that manage blood glucose levels and insulin therapy. As discussed herein, the algorithms may be referred to as an "artificial pancreas" algorithm-based system, or more generally, an artificial pancreas (AP) application. An AP application may be programming code stored in a memory device and that is executable by a processor, controller or computer device, such as a smart phone, tablet, personal diabetes management device or the like. Examples of artificial pancreas (AP) application as discussed herein provide automatic delivery of an insulin based on inputs from a blood glucose sensor input, such as that received from a CGM or the like, an inertial measurement unit (IMU), global positioning system devices and the like.

In an example, the artificial pancreas (AP) application when executed by a processor may enable a system to monitor a user's glucose values, determine an appropriate level of insulin for the user based on the monitored glucose values (e.g., blood glucose concentrations or blood glucose measurement values) and other information, such as user-provided information, such as carbohydrate intake, meal times or the like, and take actions to maintain a user's blood glucose value within an appropriate range. The appropriate blood glucose value range may be considered a target blood glucose value of the particular user. For example, a target blood glucose value may be acceptable if it falls within the range of 80 mg/dL to 140 mg/dL, which is a range satisfying the clinical standard of care for treatment of diabetes. However, an AP application as described herein may account for an activity level of a user to more precisely establish a target blood glucose value and may set the target blood glucose value at, for example, 110 mg/dL, or the like. As described in more detail with reference to the examples of FIGS. 1-7, the AP application may utilize the monitored blood glucose values and other information to generate and send a command to a wearable drug delivery device including, for example, a pump, to control delivery of insulin to the user, change the amount or timing of future doses, as well as to control other functions.

Figure 1:
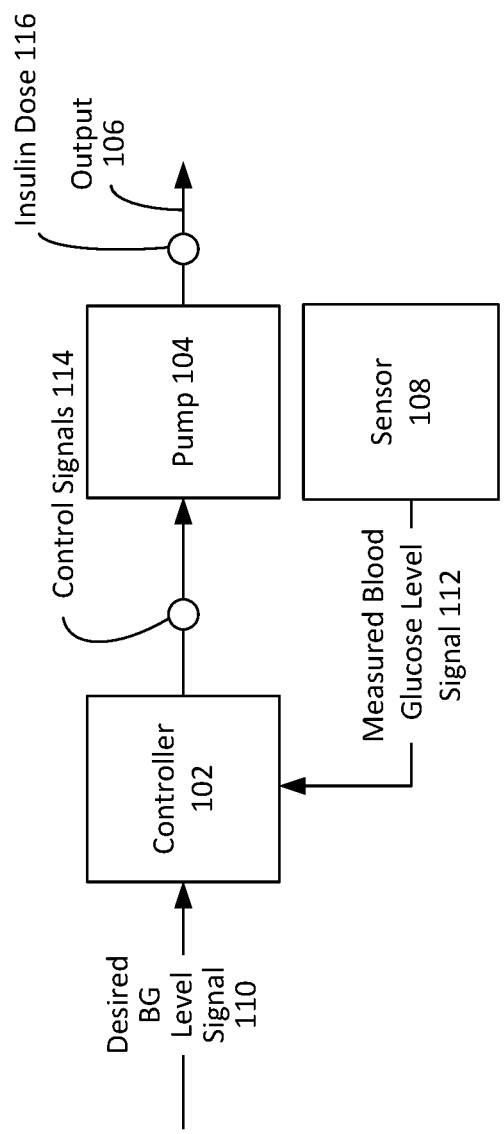
FIG. 1 illustrates an example of artificial pancreas (AP) system operable to implement the insulin delivery adjustments based on the increased activity levels of the user or detected locations of the user as discussed herein.

FIG. 1 illustrates a simplified block diagram of an example of an artificial pancreas (AP) system 100. The example AP system 100 may include a controller 102, a pump mechanism 104 (hereinafter "pump 104"), and a sensor 108. The controller 102, pump 104, and sensor 108 may be communicatively coupled to one another via a wired or wireless communication paths. For example, each of the controller 102, the pump 104 and the sensor 108 may be equipped with a wireless radio frequency transceiver operable to communicate via one or more communication protocols, such as Bluetooth®, or the like. The sensor 108 may be a glucose monitor such as, for example, a continuous glucose monitor (CGM) 108. The CGM 108 may, for example, be operable to measure BG values of a user to generate the measured BG level signal 112.

As shown in the example, the controller 102 may receive a desired blood glucose (BG) level signal 110, which may be a first signal, indicating a desired blood glucose (BG) level or range for a user. The desired BG level signal 110 may be received from a user interface to the controller or other device, or by an algorithm that automatically determines a BG level for a user. The sensor 108 may be coupled to the user and be operable to measure an approximate value of a BG level of the user. The measured BG value, the measured BG level, the measured BG level value, or the approximate measured value of the actual BG level are only approximate values of a user's BG level and it should be understood that there may be errors in the measured BG levels or values. The errors may, for example, be attributable to a number of factors such as age of the sensor 108, location of the sensor 108 on a body of a user, environmental factors (e.g., altitude, humidity, barometric pressure), or the like. The terms measured BG value and approximate measured value of the BG level may be used interchangeably throughout the specification and drawings. In response to the measured BG level or value, the sensor 108 generate a signal indicating the measured BG value. As shown in the example, the controller 102 may also receive from the sensor 108 via a communication path, a measured BG level signal 112, which may be a second signal, indicating an approximate measured value of the measured BG level of the user.

Based on the desired BG level signal 110 and the measured BG level signal 112, the controller 102 may generate one or more control signals 114 for directing operation of the pump 104. For example, one of the control signals 114 may cause the pump 104 to deliver a specified amount of insulin 116 to a user via output 106. The specified amount of insulin 116 may, for example, be determined based on a difference between the desired BG level signal 110 and the actual BG signal level 112. The specified amount of insulin may be determined as an appropriate amount of insulin to drive the measured BG level of the user to the desired BG level. Based on operation of the pump 104 as determined by the control signals 114, the user may receive the insulin 116 from the pump 104.

The AP system 100 may operate as a closed-loop system or may operate as an open-loop system. In various examples, one or more components of the AP system 100 may be incorporated into a wearable or on body drug delivery system that is attached to the user.

The simplified block diagram of the example AP system 100 provides a general illustration of the operation of the system. An example of a more detailed implementation of devices usable in such an AP system is illustrated in FIG. 2.

Various examples of an AP system include a wearable drug delivery device that may operate in the system to manage treatment of a diabetic user according to a diabetes treatment plan. The diabetes treatment plan may include a number of parameters related to the delivery of insulin that may be determined and modified by a computer application referred to as an AP application.

A wearable drug delivery device as described herein may include a controller operable to direct operation of the wearable drug delivery device via the AP application. For example, a controller of the wearable drug delivery device may provide a selectable activity mode of operation for the user. Operation of the drug delivery device in the activity mode of operation may reduce a probability of hypoglycemia during times of increased insulin sensitivity for the user and may reduce a probability of hyperglycemia during times of increased insulin requirements for the user. The activity mode of operation may be activated by the user or may be activated automatically by the controller. The controller may automatically activate the activity mode of operation based on a detected activity level of the user and/or a detected location of the user.

Figure 2:
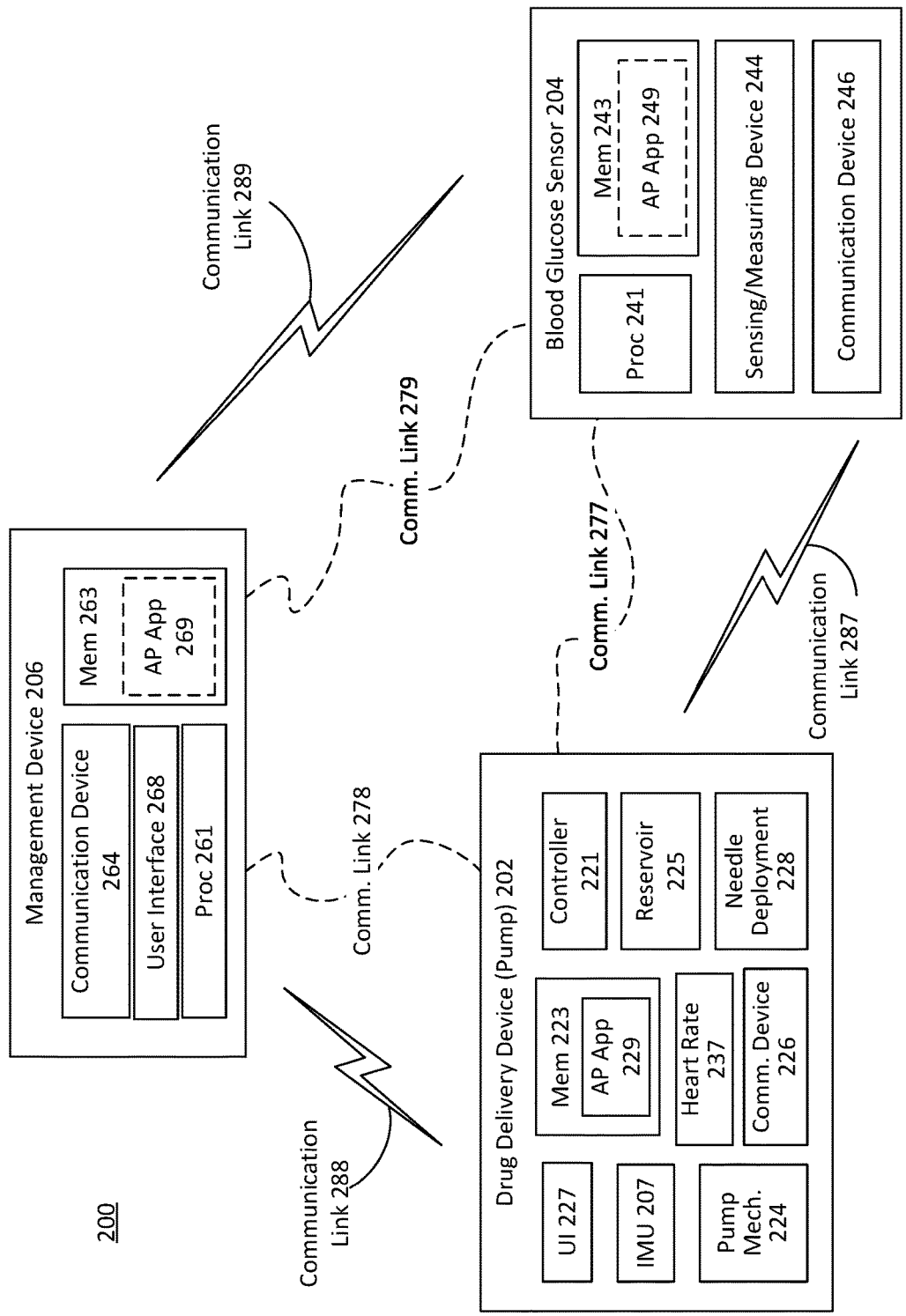
FIG. 2 illustrates an example of inertial measurement unit (IMU) operable to detect the increased activity levels as discussed herein.

FIG. 2 illustrates an example of a drug delivery system. The drug delivery system 200 may include a drug delivery device 202, a management device 206, and a blood glucose sensor 204.

In the example of FIG. 2, the drug delivery device 202 may be a wearable or on-body drug delivery device that is worn by a patient or user on the body of the user. As shown in FIG. 2, the drug delivery device 202 may include an inertial measurement unit (IMU) 207. The drug delivery device 202 may further include a pump mechanism 224 that may, in some examples be referred to as a drug extraction mechanism or component, and a needle deployment component 228. In various examples, the pump mechanism 224 may include a pump or a plunger (not shown).

The needle deployment component 228 may, for example include a needle (not shown), a cannula (not shown), and any other fluid path components for coupling the stored liquid drug in the reservoir 225 to the user. The cannula may form a portion of the fluid path component coupling the user to the reservoir 225. After the needle deployment component 228 has been activated, a fluid path (not shown) to the user is provided, and the pump mechanism 224 may expel the liquid drug from the reservoir 225 to deliver the liquid drug to the user via the fluid path. The fluid path may, for example, include tubing (not shown) coupling the wearable drug delivery device 202 to the user (e.g., tubing coupling the cannula to the reservoir 225).

The wearable drug delivery device 202 may further include a controller 221 and a communications interface device 226. The controller 221 may be implemented in hardware, software, or any combination thereof. The controller 221 may, for example, be a processor, a logic circuit or a microcontroller coupled to a memory. The controller 221 may maintain a date and time as well as other functions (e.g., calculations or the like) performed by processors. The controller 221 may be operable to execute an artificial pancreas algorithm stored in the memory that enables the controller 221 to direct operation of the drug delivery device 202. In addition, the controller 221 may be operable to receive data or information indicative of the activity of the user from the IMU 207, as well as from any other sensors (such as those (e.g., accelerometer, location services application or the like) on the management device 206 or CGM 204) of the drug delivery device 202 or any sensor coupled thereto, such as a global positioning system (GPS)-enabled device or the like.

The controller 221 may process the data from the IMU 207 or any other coupled sensor to determine if an alert or other communication is to be issued to the user and/or a caregiver of the user or if an operational mode of the drug delivery device 202 is to be adjusted. The controller 221 may provide the alert, for example, through the communications interface device 226. The communications interface device 226 may provide a communications link to one or more management devices physically separated from the drug delivery device 202 including, for example, a management device 206 of the user and/or a caregiver of the user (e.g., a parent). The communication link provided by the communications interface device 226 may include any wired or wireless communication link operating according to any known communications protocol or standard, such as Bluetooth or a cellular standard.

The example of FIG. 2 further shows the drug delivery device 202 in relation to a blood glucose sensor 204, which may be, for example, a continuous glucose monitor (CGM). The CGM 204 may be physically separate from the drug delivery device 202 or may be an integrated component thereof. The CGM 204 may provide the controller 221 with data indicative of measured or detected blood glucose (BG) levels of the user.

The management device 206 may be maintained and operated by the user or a caregiver of the user. The management device 206 may control operation of the drug delivery device 202 and/or may be used to review data or other information indicative of an operational status of the drug delivery device 202 or a status of the user. The management device 206 may be used to direct operations of the drug delivery device 202. For example, the management device 206 may be a dedicated personal diabetes management (PDM) device, a smart phone, a tablet computing device, other consumer electronic device including, for example, a desktop, laptop, or tablet, or the like. The management device 206 may include a processor 261 and memory devices 263. The memory devices 262 may store an artificial pancreas application 269 including programming code that may implement the activity mode, the hyperglycemia protection mode, and/or the hypoglycemia protection mode. The management device 206 may receive alerts, notifications, or other communications from the drug delivery device 202 via one or more known wired or wireless communications standard or protocol.

The drug delivery system 200 may be operable to implement an AP application that includes functionality to determine a movement of a wearable drug delivery device that is indicative of physical activity of the user, implement an activity mode, a hyperglycemia mode, a hypoglycemia mode, and other functions, such as control of the wearable drug delivery device. The drug delivery system 200 may be an automated drug delivery system that may include a wearable drug delivery device (pump) 202, a sensor 204, and a personal diabetes management device (PDM) 206.

In an example, the wearable drug delivery device 202 may be attached to the body of a user, such as a patient or diabetic, and may deliver any therapeutic agent, including any drug or medicine, such as insulin or the like, to a user. The wearable drug delivery device 202 may, for example, be a wearable device worn by the user. For example, the wearable drug delivery device 202 may be directly coupled to a user (e.g., directly attached to a body part and/or skin of the user via an adhesive or the like). In an example, a surface of the wearable drug delivery device 202 may include an adhesive to facilitate attachment to a user.

The wearable drug delivery device 202 may frequently be referred to as a pump, or an insulin pump, in reference to the operation of expelling a drug from the reservoir 225 for delivery of the drug to the user.

In an example, the wearable drug delivery device 202 may include a reservoir 225 for storing the drug (such as insulin), a needle or cannula (not shown) for delivering the drug into the body of the user (which may be done subcutaneously, intraperitoneally, or intravenously), and a pump mechanism (mech.) 224, or other drive mechanism, for transferring the drug from the reservoir 225, through a needle or cannula (not shown), and into the user. The reservoir 225 may be configured to store or hold a liquid or fluid, such as insulin, morphine, or another therapeutic drug. The pump mechanism 224 may be fluidly coupled to reservoir 225, and communicatively coupled to the controller 221. The wearable drug delivery device 202 may also include a power source (not shown), such as a battery, a piezoelectric device, or the like, for supplying electrical power to the pump mechanism 224 and/or other components (such as the controller 221, memory 223, and the communication device 226) of the wearable drug delivery device 202. Although also not shown, an electrical power supply for supplying electrical power may similarly be included in each of the sensor 204, the smart accessory device (if present), and the management device (PDM) 206.

In an example, the blood glucose sensor 204 may be a device communicatively coupled to the processor 261 or 221 and may be operable to measure a blood glucose value at a predetermined time interval, such as approximately every 5 minutes, or the like. The blood glucose sensor 204 may provide a number of blood glucose measurement values to the AP applications operating on the respective devices. For example, the blood glucose sensor 204 may be a continuous blood glucose sensor that provides blood glucose measurement values to the AP applications operating on the respective devices periodically, such as approximately every 5, 10, 12 minutes, or the like.

The wearable drug delivery device 202 may also include the IMU 207. The IMU 207 may be operable to detect various motion parameters (e.g., acceleration, deceleration, speed, orientation, such as roll, pitch, yaw, compass direction, or the like) that may be indicative of the activity of the user. For example, the IMU 207 may output signals in response to detecting motion of the wearable drug delivery device 202 that is indicative of a status of any physical condition of the user, such as, for example, a motion or position of the user. Based on the detected activity of the user, the drug delivery device 202 may adjust operation related to drug delivery, for example, by implementing an activity mode as discussed herein.

The wearable drug delivery device 202 may when operating in a normal mode of operation may provide insulin stored in reservoir 225 to the user based on information (e.g., blood glucose measurement values, inputs from an inertial measurement unit, global positioning system-enabled devices, Wi-Fi-enabled devices, or the like) provided by the sensor 204 and/or the management device (PDM) 206.

For example, the wearable drug delivery device 202 may contain analog and/or digital circuitry that may be implemented as a controller 221 (or processor) for controlling the delivery of the drug or therapeutic agent. The circuitry used to implement the controller 221 may include discrete, specialized logic and/or components, an application-specific integrated circuit, a microcontroller or processor that executes software instructions, firmware, programming instructions or programming code (enabling, for example, the artificial pancreas application (AP App) 229 as well as the process examples of FIGS. 5-6B) stored in memory 223, or any combination thereof. For example, the controller 221 may execute a control algorithm, such as an artificial pancreas application 229, and other programming code that may make the controller 221 operable to cause the pump to deliver doses of the drug or therapeutic agent to a user at predetermined intervals or as needed to bring blood glucose measurement values to a target blood glucose value. The size and/or timing of the doses may be programmed, for example, into an artificial pancreas application 229 by the user or by a third party (such as a health care provider, wearable drug delivery device manufacturer, or the like) using a wired or wireless link, such as 220, between the wearable drug delivery device 202 and a management device 206 or other device, such as a computing device at a healthcare provider facility. In an example, the pump or wearable drug delivery device 202 is communicatively coupled to the processor 261 of the management device via the wireless link 220 or via a wireless link, such as 208 from the sensor 204. The pump mechanism 224 of the wearable drug delivery device may be operable to receive an actuation signal from the processor 261, and in response to receiving the actuation signal and expel insulin from the reservoir 225 and the like.

The devices in the system 200, such as management device 206, wearable drug delivery device 202, and sensor 204, may also be operable to perform various functions including controlling the wearable drug delivery device 202. For example, the management device 206 may include a communication device 264, a processor 261, and a management device memory 263. The management device memory 263 may store an instance of the AP application 269 that includes programming code, that when executed by the processor 261 provides the process examples described with reference to the examples of FIGS. 1 and 3-6B. The management device memory 263 may also store programming code for providing the process examples described with reference to the examples of FIGS. 1 and 3-6B.

Although not shown, the system 200 may include a smart accessory device may be, for example, an Apple Watch®, other wearable smart device, including eyeglasses, provided by other manufacturers, a global positioning system-enabled wearable, a wearable fitness device, smart clothing, or the like. Similar to the management device 206, the smart accessory device (not shown) may also be operable to perform various functions including controlling the wearable drug delivery device 202. For example, the smart accessory device may include a communication device, a processor, and a memory. The memory may store an instance of the AP application that includes programming code for providing the process examples described with reference to the examples of FIGS. 1 and 3-6B. The memory may also as store programming code and be operable to store data related to the AP application.

The sensor 204 of system 200 may be a continuous glucose monitor (CGM) as described above, that may include a processor 241, a memory 243, a sensing or measuring device 244, and a communication device 246. The memory 243 may store an instance of an AP application 249 as well as other programming code and be operable to store data related to the AP application 249. The AP application 249 may also include programming code for providing the process examples described with reference to the examples of FIGS. 1 and 3-6B.

Instructions for determining the delivery of the drug or therapeutic agent (e.g., as a bolus dosage) to the user (e.g., the size and/or timing of any doses of the drug or therapeutic agent) may originate locally by the wearable drug delivery device 202 or may originate remotely and be provided to the wearable drug delivery device 202. In an example of a local determination of drug or therapeutic agent delivery, programming instructions, such as an instance of the artificial pancreas application 229, stored in the memory 223 that is coupled to the wearable drug delivery device 202 may be used to make determinations by the wearable drug delivery device 202. In addition, the wearable drug delivery device 202 may be operable to communicate via the communication device 226 and communication link 288 with the wearable drug delivery device 202 and with the blood glucose sensor 204 via the communication device 226 and communication link 289.

Alternatively, the remote instructions may be provided to the wearable drug delivery device 202 over a wired or wireless link by the management device (PDM) 206. The PDM 206 may be equipped with a processor 261 that may execute an instance of the artificial pancreas application 269, if present in the memory 263. The wearable drug delivery device 202 may execute any received instructions (originating internally or from the management device 206) for the delivery of insulin to the user. In this way, the delivery of the insulin to a user may be automated.

In various examples, the wearable drug delivery device 202 may communicate via a wireless communication link 288 with the management device 206. The management device 206 may be an electronic device such as, for example, a smart phone, a tablet, a dedicated diabetes therapy management device, or the like. Alternatively, the management device 206 may be a wearable wireless accessory device, such as a smart watch, or the like. The wireless links 287-289 may be any type of wireless link provided by any known wireless standard. As an example, the wireless links 287-289 may enable communications between the wearable drug delivery device 202, the management device 206 and sensor 204 based on, for example, Bluetooth®, Wi-Fi®, a near-field communication standard, a cellular standard, or any other wireless optical or radio-frequency protocol.

The sensor 204 may also be coupled to the user by, for example, adhesive or the like and may provide information or data on one or more medical conditions and/or physical attributes of the user. The information or data provided by the sensor 204 may be used to adjust drug delivery operations of the wearable drug delivery device 202. For example, the sensor 204 may be a glucose sensor operable to measure blood glucose and output a blood glucose value or data that is representative of a blood glucose value. For example, the sensor 204 may be a glucose monitor that provides periodic blood glucose measurements a continuous glucose monitor (CGM), or another type of device or sensor that provides blood glucose measurements.

The sensor 204 may include a processor 241, a memory 243, a sensing/measuring device 244, and communication device 246. The communication device 246 of sensor 204 may include an electronic transmitter, receiver, and/or transceiver for communicating with the management device 206 over a wireless link 222 or with wearable drug delivery device 202 over the link 208. The sensing/measuring device 244 may include one or more sensing elements, such as a blood glucose measurement element, a heart rate monitor, a blood oxygen sensor element, or the like. The processor 241 may include discrete, specialized logic and/or components, an application-specific integrated circuit, a microcontroller or processor that executes software instructions, firmware, programming instructions stored in memory (such as memory 243), or any combination thereof. For example, the memory 243 may store an instance of an AP application 249 that is executable by the processor 241.

Although the sensor 204 is depicted as separate from the wearable drug delivery device 202, in various examples, the sensor 204 and wearable drug delivery device 202 may be incorporated into the same unit. That is, in one or more examples, the sensor 204 may be a part of the wearable drug delivery device 202 and contained within the same housing of the wearable drug delivery device 202 (e.g., the sensor 204 may be positioned within or embedded within the wearable drug delivery device 202). Glucose monitoring data (e.g., measured blood glucose values) determined by the sensor 204 may be provided to the wearable drug delivery device 202 and/or the management device 206, which may use the measured blood glucose values to determine movement of the wearable drug delivery device indicative of physical activity of the user, an activity mode, a hyperglycemia mode and a hyperglycemia mode.

In an example, the management device 206 may be a personal diabetes manager. The management device 206 may be used to program or adjust operation of the wearable drug delivery device 202 and/or the sensor 204. The management device 206 may be any portable electronic device including, for example, a dedicated controller, such as processor 261, a smartphone, or a tablet. In an example, the management device (PDM) 206 may include a processor 261, a management device memory 263, and a communication device 264. The management device 206 may contain analog and/or digital circuitry that may be implemented as a processor 261 (or controller) for executing processes to manage a user's blood glucose levels and for controlling the delivery of the drug or therapeutic agent to the user. The processor 261 may also be operable to execute programming code stored in the management device memory 263. For example, the management device memory 263 may be operable to store an artificial pancreas application 269 that may be executed by the processor 261. The processor 261 may when executing the artificial pancreas application 269 may be operable to perform various functions, such as those described with respect to the examples in FIGS. 1 and 3-6B. The communication device 264 may be a receiver, a transmitter, or a transceiver that operates according to one or more radio-frequency protocols. For example, the communication device 264 may include a cellular transceiver and a Bluetooth transceiver that enables the management device 206 to communicate with a data network via the cellular transceiver and with the sensor 204 and the wearable drug delivery device 202. The respective transceivers of communication device 264 may be operable to transmit signals containing information useable by or generated by the AP application or the like. The communication devices 226 and 246 of respective wearable drug delivery device 202 and sensor 204, respectively, may also be operable to transmit signals containing information useable by or generated by the AP application or the like.

The wearable drug delivery device 202 may communicate with the sensor 204 over a wireless link 208 and may communicate with the management device 206 over a wireless link 220. The sensor 204 and the management device 206 may communicate over a wireless link 222. The smart accessory device, when present, may communicate with the wearable drug delivery device 202, the sensor 204 and the management device 206 over wireless links 287, 288 and 289, respectively. The wireless links 287, 288 and 289 may be any type of wireless link operating using known wireless standards or proprietary standards. As an example, the wireless links 287, 288 and 289 may provide communication links based on Bluetooth®, Wi-Fi, a near-field communication standard, a cellular standard, or any other wireless protocol via the respective communication devices 226, 246 and 264. In some examples, the wearable drug delivery device 202 and/or the management device 206 may include a user interface 227 and 268, respectively, such as a keypad, a touchscreen display, levers, buttons, a microphone, a speaker, a display, or the like, that is operable to allow a user to enter information and allow the management device to output information for presentation to the user.

In various examples, the drug delivery system 200 may be an insulin drug delivery system. For example, the wearable drug delivery device 202 may be the OmniPod® (Insulet Corporation, Billerica, Mass.) insulin delivery device as described in U.S. Pat. Nos. 7,303,549, 7,137,964, or 6,740,059, each of which is incorporated herein by reference in its entirety.

In the examples, the drug delivery system 200 may implement the artificial pancreas (AP) algorithm (and/or provide AP functionality) to govern or control automated delivery of insulin to a user (e.g., to maintain euglycemia—a normal level of glucose in the blood). The AP application may be implemented by the wearable drug delivery device 202 and/or the sensor 204. The AP application may be used to determine the times and dosages of insulin delivery. In various examples, the AP application may determine the times and dosages for delivery based on information known about the user, such as the user's sex, age, weight, or height, and/or on information gathered about a physical attribute or condition of the user (e.g., from the sensor 204). For example, the AP application may determine an appropriate delivery of insulin based on glucose level monitoring of the user through the sensor 204. The AP application may also allow the user to adjust insulin delivery. For example, the AP application may allow a user to select (e.g., via an input) commands for output to the wearable drug delivery device 202, such as a command to set a mode of the wearable drug delivery device, such as an activity mode, a hyperglycemia protect mode, a hypoglycemia protect mode, deliver an insulin bolus, or the like. In one or more examples, different functions of the AP application may be distributed among two or more of the management device 206, the wearable drug delivery device (pump) 202 or the sensor 204. In other examples, the different functions of the AP application may be performed by one device, such the management device 206, the wearable drug delivery device (pump) 202 or the sensor 204. In various examples, the drug delivery system 200 may include features of or may operate according to functionalities of a drug delivery system as described in U.S.

patent application Ser. No. 15/359,187, filed Nov. 22, 2016 and Ser. No. 16/570,125, filed Sep. 13, 2019, which are both incorporated herein by reference in their entirety.

As described herein, the drug delivery system 200 or any component thereof, such as the wearable drug delivery device may be considered to provide AP functionality or to implement an AP application. Accordingly, references to the AP application (e.g., functionality, operations, or capabilities thereof) are made for convenience and may refer to and/or include operations and/or functionalities of the drug delivery system 200 or any constituent component thereof (e.g., the wearable drug delivery device 202 and/or the management device 206). The drug delivery system 200—for example, as an insulin delivery system implementing an AP application—may be considered to be a drug delivery system or an AP application-based delivery system that uses sensor inputs (e.g., data collected by the sensor 204).

In an example, the drug delivery device 202 includes a communication device 264, which as described above may be a receiver, a transmitter, or a transceiver that operates according to one or more radio-frequency protocols, such as Bluetooth, Wi-Fi, a near-field communication standard, a cellular standard, that may enable the respective device to communicate with the cloud-based services 211. For example, outputs from the sensor 204 or the wearable drug delivery device (pump) 202 may be transmitted to the cloud-based services 211 for storage or processing via the transceivers of communication device 264. Similarly, wearable drug delivery device 202, management device 206 and sensor 204 may be operable to communicate with the cloud-based services 211 via the communication link 288.

In an example, the respective receiver or transceiver of each respective device 202, 206 or 207 may be operable to receive signals containing respective blood glucose measurement values of the number of blood glucose measurement values that may be transmitted by the sensor 204. The respective processor of each respective device 202, 206 or 207 may be operable to store each of the respective blood glucose measurement values in a respective memory, such as 223, 263 or 273. The respective blood glucose measurement values may be stored as data related to the artificial pancreas algorithm, such as 229, 249, or 269. In a further example, the AP application operating on the management device 206 or sensor 204 may be operable to transmit, via a transceiver implemented by a respective communication device, 264, 274, 246, a control signal for receipt by a wearable drug delivery device. In the example, the control signal may indicate an amount of insulin to be expelled by the wearable drug delivery device 202.

In an example, one or more of the devices 202, 204, or 206 may be operable to communicate via a wired communication links 277, 278 and 279, respectively. The cloud-based services (not shown) may utilize servers and data storage (not shown). A communication link that couples the drug delivery system 200 to the cloud-based services may be a cellular link, a Wi-Fi link, a Bluetooth link, or a combination thereof, that is established between the respective devices 202, 204, or 206 of system 200. For example, the data storage (not shown) provided by the cloud-based services may store anonymized data, such as user weight, blood glucose measurements, age, meal carbohydrate information, or the like. In addition, the cloud-based services 211 may process the anonymized data from multiple users to provide generalized information related to the various parameters used by the AP application. For example, an age-based general target blood glucose value related to activity levels or particular exercises or sports may be derived from the anonymized data, which may be helpful when a user selects an activity mode (or a hyperglycemia protect mode, or a hypoglycemia protect modes) or the system 200 automatically implements the activity mode (or the hyperglycemia protect, or the hypoglycemia protect modes). The cloud-based services may also provide processing services for the system 200, such as performing a process described with reference to later examples.

The wearable drug delivery device 202 may also include a user interface 227. The user interface 227 may include any mechanism for the user to input data to the drug delivery device 202, such as, for example, a button, a knob, a switch, a touch-screen display, or any other user interaction component. The user interface 227 may include any mechanism for the drug delivery device 202 to relay data to the user and may include, for example, a display, a touch-screen display, or any means for providing a visual, audible, or tactile (e.g., vibrational) output (e.g., as an alert). The user interface 227 may also include a number of additional components not specifically shown in FIG. 2 for sake brevity and explanation. For example, the user interface 227 may include a one or more user input or output components for receiving inputs from or providing outputs to a user or a caregiver (e.g., a parent or nurse), a display that outputs a visible alert, a speaker that outputs an audible, or a vibration device that outputs tactile indicators to alert a user or a caregiver of a potential activity mode, a power supply (e.g., a battery), and the like. Inputs to the user interface 227 may, for example, be a via a fingerprint sensor, a tactile input sensor, a button, a touch screen display, a switch, or the like. In yet another alternative, the activity mode of operation may be requested through a management device 206 that is communicatively coupled to a controller 221 of the wearable drug delivery device 202. In general, a user may generate instructions that may be stored as user preferences in a memory, such as 223 or 263 that specify when the system 200 is to enter the activity mode of operation.

Various operational scenarios and examples of processes performed by the system 200 are described herein. For example, the system 200 may be operable to implement process examples related to an activity mode including a hyperglycemia protect mode and a hypoglycemia protect mode as described in more detail below.

In an example, the drug delivery device 202 may operate as an artificial pancreas (AP) system (e.g., as a portion of the AP system 100) and/or may implement techniques or an algorithm via an AP application that controls and provides functionality related to substantially all aspects of an AP system or at least portions thereof. Accordingly, references herein to an AP system or AP algorithm may refer to techniques or algorithms implemented by an AP application executing on the drug delivery device 202 to provide the features and functionality of an AP system. The drug delivery device 202 may operate in an open-loop or closed-loop manner for providing a user with insulin.

Additional features may be implemented as part of the AP application such as the activity mode, the hyperglycemia mode, the hypoglycemia mode, or the like. For example, the drug delivery device 202 when programming code is executed that enables the activity mode, hyperglycemia mode, hypoglycemia mode or the like of the AP application. As the AP application including the programming code for the activity mode, the hyperglycemia mode, and the hypoglycemia mode is executed, the AP application may adjust operations, such as detecting motion or movement of the wearable drug delivery device that is indicative of physical activity of the user. For example, motion and movement of the wearable drug delivery device 202 that induces motions characteristic of physical activity of the user (e.g., movements, such as jumping, dancing, running, weightlifting, cycling or the like) may be detected by the IMU 207. In addition, the IMU 207, as described in more detail with reference to FIG. 3, may include a global positioning system that may detect a location of the wearable drug delivery device 202. Alternatively, or in addition, the wearable drug delivery device 202 may also obtain location information by utilizing Wi-Fi location services obtained via communication device 226 enabling the controller 221 to determine the location of the wearable drug delivery device 202.

In an example, the AP algorithm may learn from repeated interaction with the user who may input an indication at particular times that they are about to perform physical activity. Alternatively, or in addition, the wearable drug delivery device 202 may upon detection of a particular location (e.g., gym, sports field, stadium, track, or the like) determine that the user is about to increase their physical activity. In an operational example, the controller 221 may be operable to receive a location associated with the wearable drug delivery device 202 from the IMU 207 or Wi-Fi location services provided via the communication device 226. The controller may obtain locations of physical activity from the memory 223 and be operable to compare the received location to locations of physical activity obtained from the memory. The controller 221, based on a result of the comparison indicating that the location associated with the wearable drug delivery device is substantially the same as a location in the locations of physical activity obtained from the memory, may indicate that an activity mode threshold has been exceed. In which case, if not having already done so, the controller 221 may initiate an activity mode or a hypoglycemia protect mode.

Figure 3:
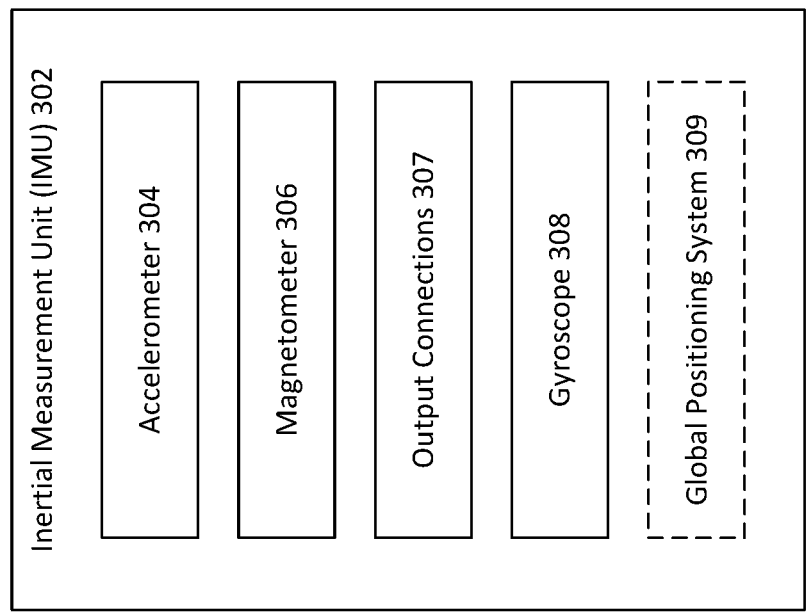
FIG. 3 illustrates an example of drug delivery device operable to implement the techniques and processes described herein.

It may be helpful to describe the number of components included in the IMU 207 that provide motion and movement measurement data or values to the controller 221. An example of an inertial measurement unit (IMU) is shown in FIG. 3. The IMU 302 may include an accelerometer 304, a magnetometer 306, output connections 307, and a gyroscope 308. The IMU 302 may optionally include a global positioning system component 309.

The output connections 307 enable the IMU 302 to be coupled other components of a wearable drug delivery device, such as 202 of FIG. 2. The IMU 302 may combine the features and capabilities of the accelerometer 304, the magnetometer 306, and the gyroscope 308 for detecting various operational parameters of the wearable drug delivery device. In various examples, the IMU 302 may be integrated into a drug delivery device or system such as, for example, a wearable or on-body drug delivery device. In various examples, the IMU 302 may be used for detecting various parameters related to activity of a user and for enabling the activity mode (and/or the hyperglycemia mode or the hypoglycemia mode) disclosed herein. In various examples, the device or system in which the IMU 302 is integrated may also dynamically adapt activity mode parameters based on the user's response to an activity. The activity, for example, may be a user indicated activity or may be an activity detected based on a level of activity measured by, for example, the accelerometer 304, the magnetometer 306, or the gyroscope 308.

For example, the accelerometer 304 may generate one or more signals indicative of, for example, a detected or measured acceleration force. The magnetometer 306 may generate one or more signals indicative of, for example, a detected or measured magnetic field. The gyroscope 308 may generate one or more signals indicative of, for example, an orientation of the gyroscope 308 or the IMU 302, or a device in which either component is integrated. The signals generated by the accelerometer 304, the magnetometer 306, and the gyroscope 308 may be provided to other components and devices (e.g., the processor or controller 221 of FIG. 2) and/or may be stored (e.g., within a non-transitory computer readable memory). In various examples, the IMU 302 may detect a motion, a movement, or a position of a device in which it is incorporated (or of a user wearing the device in which the IMU 302 is integrated).

The IMU 302 may also be equipped with a global positioning system (GPS) component 309 that receives signals from which a location of the IMU 302 may be determined. The determined location may be provided to the controller 221 of the wearable drug delivery device 202 via a communication link 277 or 287 as well as to the processor 261 of the management device 206. In addition, the blood glucose sensor 204, if executing an instance of the AP application, such as 249, may also receive a signal from the GPS 309.

Figure 4:
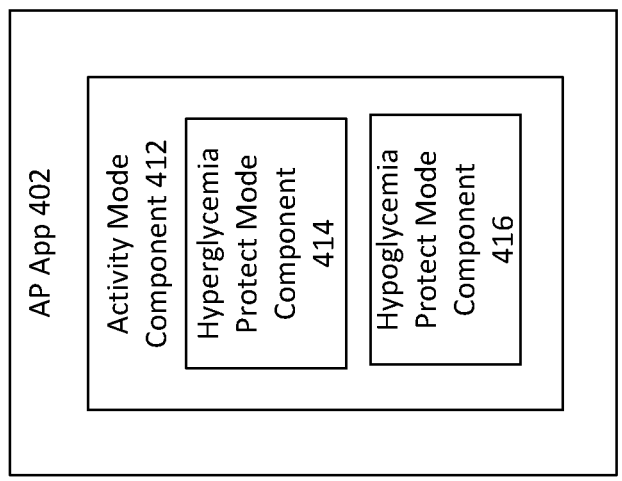
FIG. 4 illustrates an example of components of the AP application with respect to examples related to an activity mode, a hyperglycemia protect mode, and a hypoglycemia protect mode.

FIG. 4 illustrates an example of components of the AP application. The AP application 402 may be non-transitory computer-readable programming code stored in the memory of a device such as management device 206, wearable drug delivery device 202 or blood glucose sensor 204. Each of the management device 206, the wearable drug delivery device 202, or the blood glucose sensor 204 may execute their individual instances of the AP application 402 (as shown in and discussed with reference to the example of FIG. 2). The AP application 402 may provide functions, such as managing the daily delivery of insulin to a user as described with reference to the examples of FIGS. 1 and 2. Additional examples of functions provided by the AP application 402 are described in U.S. patent application Ser. No. 15/359,187, filed Nov. 22, 2016 and Ser. No. 16/570,125, filed Sep. 13, 2019, which are both incorporated herein by reference in their entirety.

The activity mode component 412 may be additional programming code that may be a plug-in to the AP application 402. The activity mode component 412 may provide functions related to activity mode, such as those mentioned above, that responds to the detection of movement related to physical activity of a user wearing a wearable drug delivery device, such as 202 of FIG. 2. Within the activity mode component 412 may be additional components, such as a hyperglycemia protect mode component 414 and a hypoglycemia protect mode component 416.

The hyperglycemia protect mode component 414 may provide additional functions, constraints and limits to the insulin dosages provided while the activity mode is initiated to protect a user from having blood glucose measurements that exceed clinically acceptable blood glucose levels (e.g., greater than or approximately equal to 180 mg/dL). Conversely, the hypoglycemia protect mode component 416 may provide additional functions, constraints and limits to the insulin dosages provided while the activity mode is initiated to protect a user from having blood glucose measurements that fall below clinically acceptable blood glucose levels (e.g., less than or approximately equal to 70 mg/dL).

In an example, operation of the AP application may be operable to receive inputs from a user, a blood glucose sensor, such as 204 of FIG. 2 or 108 of FIG. 1, other devices, such as a management device 206 or wearable drug delivery device, or obtain data from a memory, such as 223 or the 263. In response to receiving inputs from the IMU 207, the AP application 402 may respond to the inputs by initiating the functions of the activity mode component 412. For The activity mode component 412 may provide additional inputs, add weightings to parameters (e.g., weightings to the calculation of total daily insulin (TDI), the basal dosages of a user, bolus dosages, or the like) used in the calculations of the doses of insulin to be delivered to the user. The determined location by the GPS 309 may be flagged by a user as a location at which physical activity takes place, such as a gym, a sports field, or the like.

While the foregoing examples described the hardware and software components that may be used to provide an AP application 402 augmented with functionality provided by an activity mode, a hyperglycemia protect mode and a hypoglycemia protect mode, each of the respective modes of operation may present different processes to provide the respective functionality.

Figure 5:
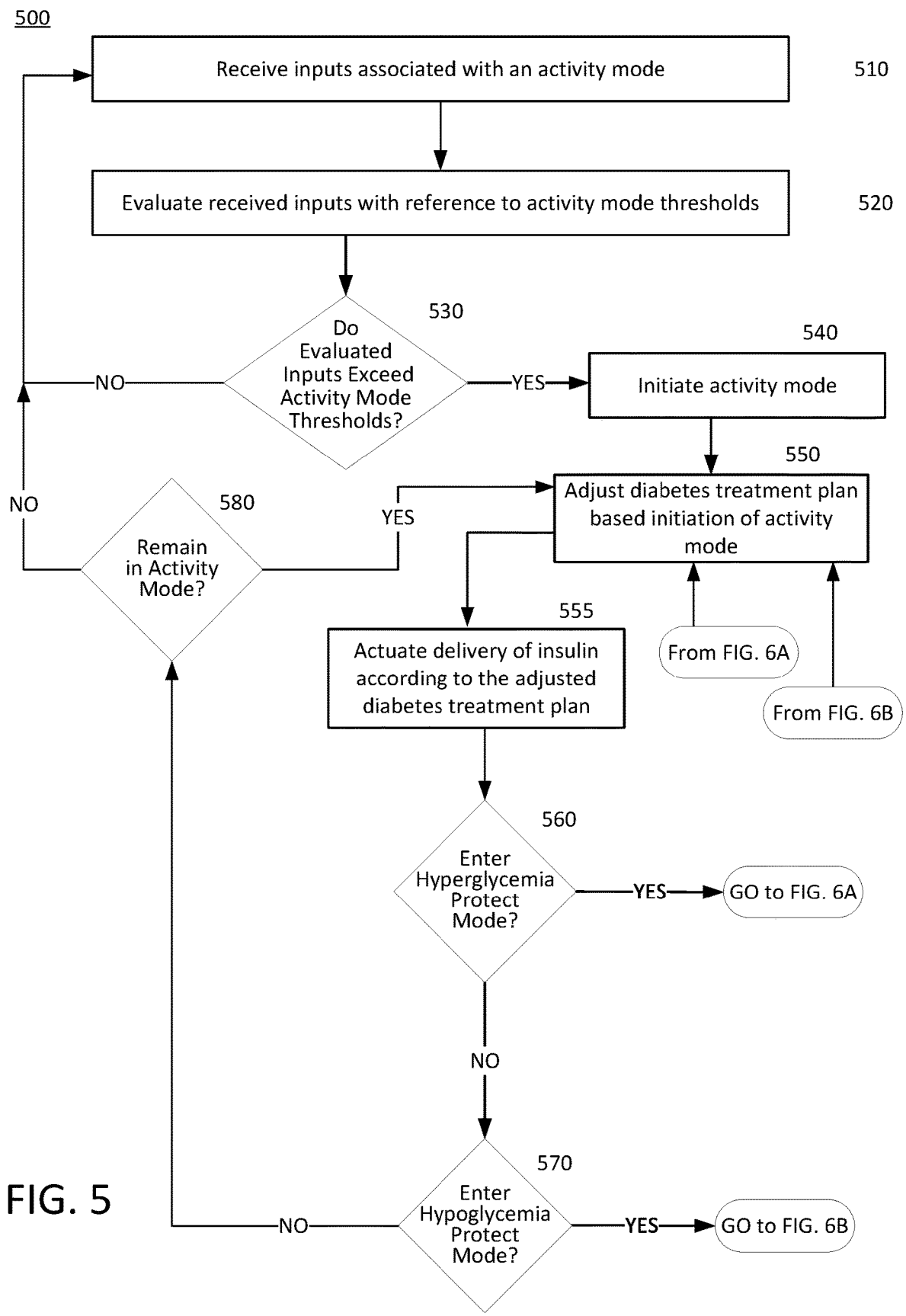
FIG. 5 illustrates an example process of the activity mode.

The AP application 402 of FIG. 4 may operate in an activity mode to reduce a likelihood of an occurrence of hypoglycemia and hyperglycemia. FIG. 5 illustrates an example process of the activity mode. The example process of FIG. 5 is described below with reference to the system example of FIG. 2.

As disclosed herein, when the drug delivery device 202 in the example of FIG. 2 may operate as a closed loop system under control of the AP application. In an example, a close loop system may use a continuous glucose monitor to provide blood glucose measurements and use of the AP application to determine insulin dosing requirements and automated delivery as shown in the example of FIG. 2) As a result, much of the burden is removed from the user to keep insulin levels of the user within a range appropriate for the particular user given, for example, the user's insulin on board, insulin sensitivity, or the like. The closed loop operation may be provided in part by monitoring blood glucose (BG) levels of the user occasionally (e.g., periodically) to determine an amount of insulin to deliver to the user, without user intervention. By closely monitoring BG levels, large and/or frequent fluctuations in BG levels of the user may be avoided. However, even during this closed loop operation by a drug delivery device, such as 202, additional monitoring as provided by the activity mode plug-in may ensure BG levels do not fall below certain safe levels, especially when a user is engaged in physical activity, such as exercising, participating in sports, dancing and the like.

For example, the activity mode disclosed herein may be used for reducing the probability of hypoglycemia due to increased insulin sensitivity. In an example, the activity mode disclosed herein may be used to manage general increases of average blood glucose to prevent hypoglycemia during times of high glucose variability. In addition, the activity mode may reduce the probability of hyperglycemia due to increased insulin requirements. The activity mode may also be used to reduce alarm requirements (cause alarms to occur earlier or later) to prevent excessive periods of high glucose concentrations during times of increased insulin resistance by informing the user initiating changes in manual or automatic insulin delivery. In an example, multiple settings of the activity mode (or any additional or sub-mode thereof) may be available to set operation to different degrees of conservativeness or aggressiveness.

In closed loop operation, the AP application may manage a user's diabetes treatment plan using various parameters and functions, such as cost functions and the like, as discussed in described in U.S. patent application Ser. No. 15/359,187, filed Nov. 22, 2016 and Ser. No. 16/570,125, filed Sep. 13, 2019, which are both incorporated herein by reference in their entirety. As an example, a conservative mode of operation may include use of a setpoint equal to approximately 120 to 150 mg/dL, setting a maximum insulin delivery equal to approximately 1 to 3 times the user's basal rate, and setting the input basal to the AP algorithm equal to approximately 50% to 90% of the user's entered basal rate. Alternatively, an aggressive mode of operation may include use of a setpoint equal to approximately 100 to 120 mg/dL, setting a maximum insulin delivery to at most approximately 3 to 6 times the user's basal over approximately 3 to 6 hours, and reducing the hyperglycemia alarm threshold(s) to triggering alarms for any glucose values above approximately 250 to 350 mg/dL for more than approximately 15 minutes to 60 minutes.

In the process 500, the AP application may use settings similar to the above insulin delivery parameters and alarm thresholds as a baseline during daily management of a user's diabetes treatment plan (i.e., without the initiation of activity mode). While the AP application is executing by a processor or controller, such as 221, the AP application may receive inputs associated with the activity mode at 510. The inputs may be received from several different sources including from the controller 221. For example, the AP application executing on the drug delivery device 202 may monitor inputs from the IMU 207, the heart rate monitor 237, and the user interface 227 for signals or indications associated to activity mode. The outputs from the IMU 207 and/or the heart rate monitor 237 may include timestamps so the controller 221 may determine a duration of the physical activity indicated by the received inputs.

Alternatively, at 510, the drug delivery device 202 may, for example, receive via the user interface 227 a selection specifying activation of the activity mode of operation via the user interface 227. Alternatively, the AP application executing on the wearable drug delivery device may determine the occurrence of increased physical activity based on signals indicating, for example, increased heart rate or pulse rate received from the heart rate monitor 237, movement indicators from the IMU 207, or a combination of both.

Based on the signals received from the IMU, heart rate monitor 237 and the user interface, the AP application may evaluate the received inputs to determine whether to initiate the activity mode at 520. In various examples, the evaluation of the received inputs, at 520, may include an evaluation of default values for duration and an intensity level of the physical activity indicated by the received inputs. For example, the AP application may receive an indication of a heart rate over a predetermined threshold, e.g., 50-70 percent of the maximum age-appropriate heart rate or the like, an accelerometer reading indicating motion exceeding a walking pace, gyroscopic readings indicating motion in up/down and lateral directions, or the like for a period of time that exceeds an activity duration threshold. Alternatively, or in addition, the user may specify an amount of time and/or a different activity intensity level when the activity mode of operation is entered manually. For example, the duration of the activity mode of operation may be a timed session (e.g., 1 hour, 2 hours, a common duration of a sports event (e.g., 2.5 hours for a baseball game, or the like) or may be turned off manually by a user or caregiver.

For example, the AP application may evaluate the received inputs against activity mode thresholds stored in a memory, such as 223. The activity mode thresholds may be based on user history accumulated over days, months or years, user preference settings, or as a default, clinical information based on the user's age, weight, height and the like. In another example, the evaluation at 520 may include comparing the monitored indicators to activity mode thresholds set by the user. In various examples, the AP application may automatically initiate the activity mode of operation based on activity of the user detected by the IMU 207.

In an example, the controller 221 may retrieve the activity mode thresholds from a memory, such as 223. The controller 221 may determine a duration of an indication of physical activity. The controller 221 may compare the determined duration of the indication of physical activity to a default duration value from among the retrieved activity mode thresholds. Based on a result of the comparison, the controller 221 may indicate that the duration of the indication of physical activity exceeds an activity mode threshold for duration of physical activity. In response to the indication that the duration of the indication of physical activity exceeds an activity mode threshold for duration of physical activity, output an instruction to initiate activity mode. Alternatively, the activity mode thresholds may be set by a user, who may use default or user specified presets that assign a set of operational parameters that may be varied for an activity.

In another example, the AP application may monitor and access a data storage (e.g., a memory), which may contain a spreadsheet, a calendar, or the like, for scheduling information related to events or physical activity input by a user as either additional received inputs or as the sole received inputs at 510. The scheduling information may include a schedule of physical activity or events in which the user participates or that may affect diabetes management, such as airplane travel, conferences, holidays, or the like that the user is participating in during a period of time (e.g., a day, hour, month, week, or year). The scheduling information may include physical fitness (i.e., exercise) classes, sports events, marathon schedules, travel arrangements, conference dates (and agenda), and the like. The AP application may be operable to access (according to user permissions) the schedule and evaluate scheduled events (e.g., travel, conferences, birthdays) or scheduled physical activity.

After accessing the scheduling information stored in the data storage, the evaluation of the scheduled events or scheduled physical activity by the AP application at 520 may include comparing dates and times with a current time and date maintained by the controller 221. Based on the results of the comparison, identify an event and a scheduled physical activity that a user is participating. The controller 221 executing the AP application may generate an alert, either via the user interface 227 or cause a signal to be transmitted to the management device 206, for presentation of a prompt requesting confirmation of initiation of the activity mode.

The AP application may at 530 determine whether the inputs evaluated at 520 exceed any activity mode thresholds. If the determination is NO, the process 500 may return to 500 and continue. Alternatively, should the AP application determine that YES, the evaluated inputs exceed the activity mode thresholds, the process 500 may proceed with the AP application initiating the activity mode at 540.

In yet another example, the user may also schedule via the user interface 227 activation of the activity mode of operation for a certain future day or time in which case the evaluation at 520 may be whether the physical activity was scheduled in which case the result of the evaluation is that the activity mode threshold is exceeded.

In response to the initiation of the activity mode at 540, the process 500 at step 550 may modify or adjust the diabetes treatment plan. For example, the AP algorithm executing on the drug delivery device 202 may recommend administering or may automatically administer a correction bolus prior to the expected increased period of insulin requirements based on, for example, a scheduled time of event, a determined glucose value, a determined lack of insulin on board, or any combination thereof.

For example, the AP application executed by the controller 221 may adapt or modify and adjust the parameters of a diabetes treatment plan according to the adjusted or modified parameters as the activity mode of operation is implemented multiple times over a period of time based on actual learned patient response to any parameter associated with a particular activity mode of operation. For example, the AP application, while in the activity mode, may continue to receive inputs related to the user's diabetes treatment plan. For example, the received inputs may include determined glucose values, determined glucose rates or change, motion or activity detected by components (shown and described with reference to the example of FIG. 3) of the IMU 207, and/or inputs from other sensors integrated within or otherwise coupled to the drug delivery device 202. The AP application may continue to evaluate and process the received inputs utilizing AP application algorithms and functions adjusted based on the activity mode, but also the daily operation of the AP application. The AP application may use the received inputs to determine whether there is a need to adjust diabetes treatment plan parameters (e.g., an amount of bolus dosage, a calculation of insulin on board, total daily insulin, timing of insulin delivery, or the like) over time. The AP application in response to the adjusted parameters of the diabetes treatment plan may modify an amount of insulin to be delivered by the pump mechanism 224.

At 555, the AP application may, in response to the adjusted parameters of the diabetes treatment plan, cause the controller 221 to actuate the pump mechanism 224 to deliver insulin according to the adjusted diabetes treatment plan (which was adjusted in 550).

In an example, when the AP application utilizes the scheduled events or physical activity to initiate the activity mode, the AP application may look at scheduled events or physical activity that are scheduled in the future (e.g., several hours or the like in the future). In response to evaluating the future scheduled events or physical activity, the AP application may, prior to the occurrence of the scheduled activity or event, initiate activity mode in advance and begin adjusting the diabetes treatment plan. For example, the AP application may determine that the amount of insulin on board (e.g., prior to exercise scheduled for the user) is to be reduced to meet limits established for the user. In a specific example, when an activity may be scheduled to begin, for example, at 10:00 am, the drug delivery device 202 may start the activity mode of operation at, for example, 8:30 am to allow time for the user's blood glucose to elevate and to reduce an amount of insulin on board (i.e., within the body of the user). By starting the activity mode in advance of the scheduled event or physical activity, the AP application may either suspend delivery of insulin or reduce an amount of insulin scheduled to be delivered to allow the amount of insulin on board to diminish and the measured blood glucose value to increase. Alternatively, the scheduled event may be an event for which the increase in insulin resistance is expected. As a result, the AP application executing on the drug delivery device 202 may initiate the activity mode of operation prior to an expected increase in insulin resistance in order to adjust the diabetes treatment plan of the user to increase the amount of insulin on board prior to the event for which the increase in insulin resistance is expected. The foregoing adjustments to the diabetes treatment plan may be in response to monitoring the scheduled events.

The techniques or processes 500 implemented by the AP application related to the activity mode may also implement a hyperglycemia protect mode and a hypoglycemia protect mode. For example, an activity mode may be operable through the hypoglycemia protect mode to reduce the potential for an occurrence of hypoglycemia during periods of increased insulin sensitivity such as, for example, during exercise or other moderate-to-intense physical activity. In addition, the activity mode may, for example, be operable to reduce a likelihood of an occurrence of hyperglycemia during times of increased insulin requirements, such as, for example, when the user is suffering from an illness (stress), is on a long plane flight (environmental conditions associated with air travel such as reduced air pressure that affects glucose monitoring, reduced ability to control diet, and the like), or the like. As an example, a conservative mode of operation may include use of a setpoint equal to approximately 120 to 150 mg/dL, setting a maximum insulin delivery equal to approximately 1 to 3 times the user's basal rate, and setting the input basal to the AP algorithm equal to approximately 50% to 90% of the user's entered basal rate. Alternatively, an aggressive mode of operation may include use of a setpoint equal to approximately 100 to 120 mg/dL, setting a maximum insulin delivery to at most approximately 3 to 6 times the user's basal over approximately 3 to 6 hours, and reducing the hyperglycemia alarm threshold(s) to triggering alarms for any glucose values above approximately 250 to 350 mg/dL for more than approximately 30 minutes.

The activity mode of operation may include or may separately specify a hypoglycemia mode of operation and/or a hyperglycemia mode of operation. When operating in the activity mode, the AP algorithm may also implement the hypoglycemia protection mode of operation and the hyperglycemia protection mode of operation.

At 560, the AP application may process blood glucose measurements received from the blood glucose sensor 204 over time, amounts of insulin delivered over time according to the diabetes treatment plan of the user, and calculate and analyze trends determined related to insulin delivery and the blood glucose measurements. Based on the processing, the AP application may evaluate whether a hyperglycemia protect mode is to be entered, such as if the AP application determines a persistently elevated raw glucose concentration or trend during increasing insulin delivery, or unchanging raw glucose concentration or trend during reduced insulin delivery, or elevated raw glucose value or trend over significant periods of time regardless of insulin delivery, or the like. For example, the AP application may enter hyperglycemia mode in cases where persistently high glucose values are detected even if a significant amount of insulin has been delivered. Based on the result of the evaluation, the AP application may determine that YES, a hyperglycemia protect mode is to be entered and the process 500 proceeds as a precautionary measure to the process shown in FIG. 6A. In an example, the AP application may determine to enter the hyperglycemia protect mode based on an input received from a calendar or user input. For example, the user may be scheduled for 10:00 am airline flight, in such as case, the drug delivery device 202 may initiate the activity mode of operation at 8:00 am to reduce the user's glucose and to increase the amount of insulin on board and in preparation for entering (i.e., the determination at 560 is YES) the hyperglycemia protect mode.

In an operational example, the controller 221 (or a processor) may be operable to receive blood glucose measurements from the blood glucose sensor 204. The controller 221 (or processor) may process the blood glucose measurements. The processing may reveal the blood glucose measurements are increasing toward exceeding a maximum blood glucose set point. The maximum blood glucose set point may be a blood glucose value that the AP application (or the user manually) sets as a maximum upper limit of a blood glucose value for the user. Based on an indication that the blood glucose measurements are increasing toward exceeding the maximum blood glucose set point, the controller may enter the hyperglycemia protect mode. Alternatively, or in addition, the AP application executing on the controller may generate an alarm signal indicating that the blood glucose measurements are increasing toward exceeding the maximum blood glucose set point to enable the user to take remedial action.

Conversely, if the AP application determines, at 560, NO, the hyperglycemia protect mode does not need to be entered and the process 500 proceeds to 570.

At 570, the AP application may process blood glucose measurements received from the blood glucose sensor 204 over time, amounts of insulin delivered over time according to the diabetes treatment plan of the user, and trends determined related to insulin delivery and the blood glucose measurements. Based on the processing, the AP application may evaluate whether a hypoglycemia protect mode is to be entered, such as if the AP application determines a persistently reduced raw glucose concentration or trend during decreasing insulin delivery, or unchanging raw glucose concentration or trend during increased insulin delivery or reduced raw glucose value or trend over significant periods of time regardless of insulin delivery, or the like. For example, the AP application may determine to enter hypoglycemia protect mode if the measured blood glucose value continues to drop despite reduced insulin delivery or suspension. Based on the result of the evaluation, the AP application may determine that YES, a hypoglycemia protect mode is to be entered and the process 500 proceeds as a precautionary measure to the process shown in FIG. 6B.

In an operational example, the controller 221 (or a processor) may be operable to receive blood glucose measurements from the blood glucose sensor 204. The controller 221 (or processor) may process the blood glucose measurements. The processing may reveal the blood glucose measurements are decreasing toward a minimum blood glucose set point. The minimum blood glucose set point may be a blood glucose value that the AP application (or the user manually) sets as a minimum lower limit of a blood glucose value for the user. Based on an indication that the blood glucose measurements are decreasing toward falling below the minimum blood glucose set point, the controller may enter the hypoglycemia protect mode. Alternatively, or in addition, the AP application executing on the controller may generate an alarm signal indicating that the blood glucose measurements are decreasing toward falling below the minimum blood glucose set point to enable the user to take remedial action.

Conversely, if the AP application determines NO, the hypoglycemia protect mode does not need to be entered and the process 500 proceeds to 580.

The hypoglycemia and hyperglycemia protection modes may either, in a first scenario, be modes of operation that are distinct from one another, (i.e., that are separately selectable or automatically entered into) or, in a second scenario, may be sub-modes of operation under the activity mode of operation and may be entered into automatically during execution of the activity mode of operation. Under either scenario, the techniques and devices disclosed herein enable operation according to these modes (e.g., activity mode, hypoglycemia protection mode or hyperglycemia protection mode) of operation to provide the protection and risk management benefits and advantages of an AP application enabled with these additional modes of operation as disclosed herein.

At 580, the AP application determines whether to remain in activity mode. For example, if the user set duration for activity mode has not expired the AP application may continue operating in activity mode. Alternatively, the received inputs from the IMU 207 or heart rate monitor 237 may continue to indicate physical activity. As a result of either the set duration not expiring or the continued indication of physical activity, the determination at 580 may be YES and the process 500 returns to 550 for adjustment of the diabetes treatment plan. Note that the adjustment of the diabetes treatment plan may be on-going as updated blood glucose measurements continue to be received by the AP application and are evaluated. Alternatively, the determination at 580 may be NO, do not remain in activity mode in which case the process 500 returns to 510 to receive inputs associated with the activity mode to determine if the user will be participating in other physical activity.

The increased activity may be detected using indicators such as, for example, increased heart rate or pulse rate, and comparing the monitored indicators to threshold activity levels. The drug delivery device 202 may adjust monitoring of the indicators and any thresholds based on learned behavior and patterns of the user.

Figure 6A:
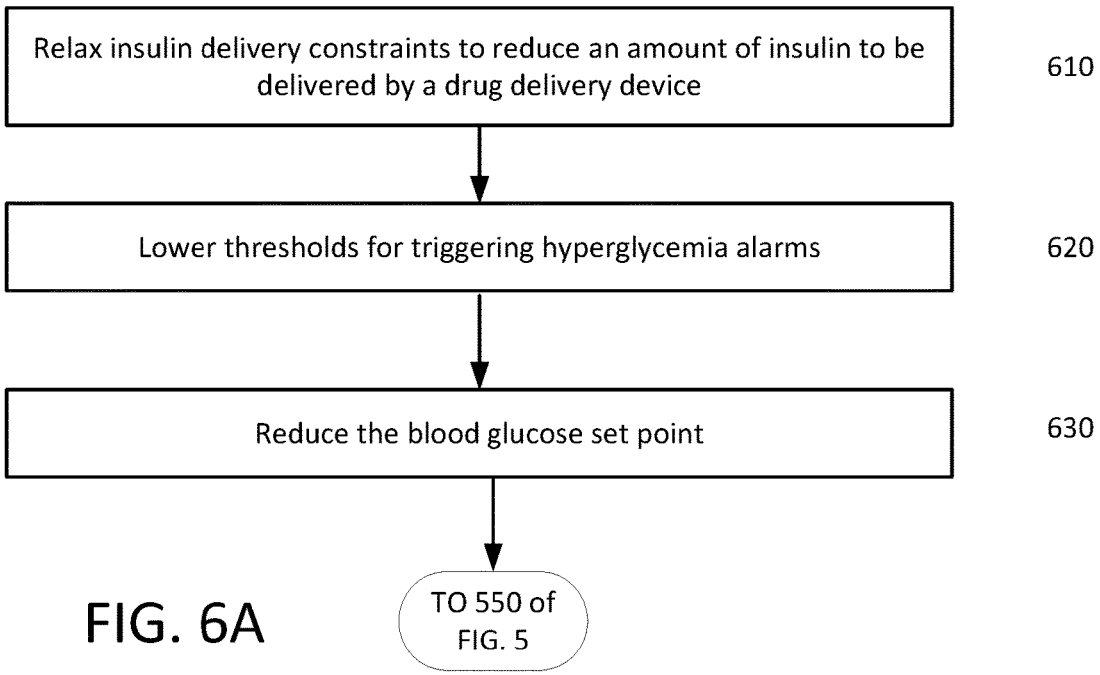
FIG. 6A illustrates an example process implemented when the AP application initiates a hyperglycemia protect mode.

FIG. 6A illustrates an example process implemented when the AP application initiates a hyperglycemia protect mode. The process 600 enabled by the AP application when executed by a controller or process may implement a hyperglycemia protect mode. The hyperglycemia protect mode may involve relaxation of insulin delivery constraints at 610. In the example, the insulin delivery constraints may be limited over a specified or predetermined period of time. In another example, the hyperglycemia protect mode of operation may, at 610, relax the insulin delivery constraints if the user continues having insulin deliveries limited by the relaxed constraints during earlier activations of the hyperglycemia protect mode of operation.

The process 600 may also proceed to 620 at which the thresholds for triggering hyperglycemia alarms may be lowered. In addition, the process 600 may enable the blood glucose setpoint (i.e., the user's target blood glucose level) to be reduced (630).

The limits of the AP system's (or any algorithm executed by the drug delivery system 202) total possible insulin delivery over a duration may change gradually, instead of instantly, based on an observed increase in mean glucose concentration values. In other examples, the hyperglycemia mode may change parameters or inputs of the AP application (e.g., a cost function or gain) to cause the AP application to be less conservative and/or more aggressive in the determination of insulin dosage amounts and in the delivery schedules of the determined insulin dosage amounts.

Figure 6B:
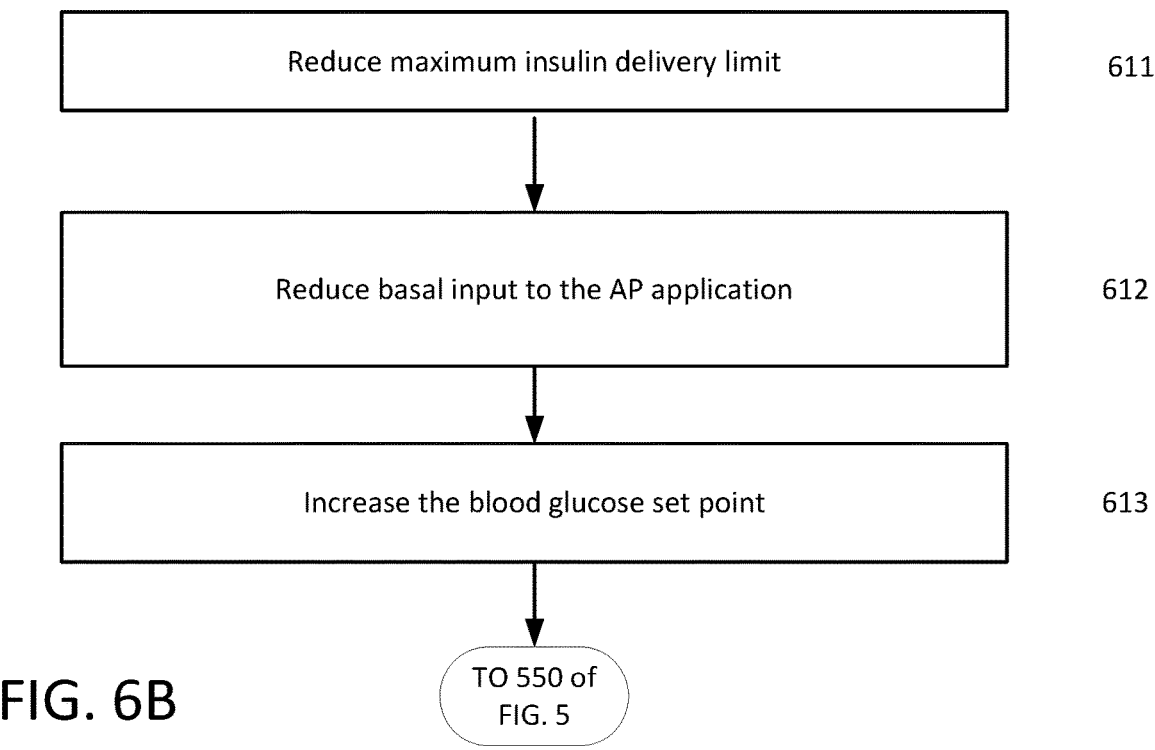
FIG. 6B illustrates an example process implemented when the AP application initiates a hypoglycemia protect mode.

FIG. 6B illustrates an example process implemented with the AP application initiates a hypoglycemia protect mode. The process 601 enabled by the AP application when executed by a controller or process may implement a hyperglycemia protect mode. The hypoglycemia protect mode process 601 may include reducing maximum insulin delivery limit (611). The maximum insulin delivery limit may be a maximum amount of insulin the AP application is permitted to deliver to a user in a given period of time, such as, for example, 8, 24, 48 or 72 hours, or the like. The reduced maximum insulin delivery limit at 611 may be maintained, for example, over a specified or predetermined period of time. The maximum insulin delivery limit may be personalized to the user such as a multiple of the user's basal rate. In other examples, the hypoglycemia mode of operation may change parameters or inputs of the AP application (e.g., cost function or gain) implemented by the drug delivery device 202 to cause the AP application to be more conservative.

At 612, the process 601 may reduce the basal input to the AP application, for example, being executed by a controller 221 of the drug delivery device 202. The reduced basal input may indicate to the AP application that a reduced basal insulin dosage that may be different than the basal input indicated by the user. For example, the basal input may be a basal insulin delivery value input by a user as part of a user's standard basal insulin dosage setting by the user, who may not have all the blood glucose measures, calculations of insulin on board, insulin sensitivity, other diabetes treatment plan information, or the like that the AP application has or is able to access and process. In response to being provided with the basal input, the AP application may correspondingly process the basal input and determine to reduce the amount of insulin delivery even when the user's standard basal insulin dosage settings as indicated by the provided basal input remain substantially the same.

At 613, the AP application may increase a blood glucose setpoint. For example, a user may have their blood glucose setpoint set at 100 mg/dL, in step 613, the AP application when in the hypoglycemia protect mode, may increase the blood glucose setpoint to 130 mg/dL or greater. As noted above, hypoglycemia may be induced by intense physical activity. In the hypoglycemia protect mode, the AP algorithm executing on the drug delivery device 202 may as part of any of steps 611-613, recommend with a prompt presented on a user interface or the like that the user intake carbohydrates prior to any planned exercise or during exercise based on, for example, a scheduled time of exercise, a detected glucose rate, a determined amount of insulin on board, or any combination thereof.

In an example, the hypoglycemia protect mode of operation may further include a step of reducing insulin delivery if the user experiences increased instances of hypoglycemia during earlier activations of the hypoglycemia protect mode of operation.

To ensure proper use of the available hypoglycemia protect mode, the drug delivery device 202 may ensure entry into this available mode of operation even when the user forgets to manually specify activation (e.g., forgetting to request the mode of operation prior to exercising).

In further examples, alerts may be provided by the AP application may generate alerts for output the user regarding the hypoglycemia protect mode of operation or automatic entry into the mode may occur when, for example, increased activity is detected, and the mode is not selected and/or when a location associated with increased activity levels is detected and the mode is also not selected for output via the user interface 227 or user interface 268 of the management device 206. Under these scenarios, the drug delivery device 202 may alert the user to the detected conditions, as described herein. To facilitate entry into the hypoglycemia protect mode of operation even when not specified by the user, the AP application executing on the controller 221 of the drug delivery device 202 may implement techniques to monitor the following conditions and provided feedback to the user. For example, the AP application may determine user activity is increased based upon motion data and biometric sensing, for example, by the IMU 207 or other sensor; and the user is in a geographic location where increased activity has been previously detected (e.g., based on increased activity in certain recognized locations).

By detecting activity levels and locations (e.g., via a GPS device, Wi-Fi location service or device, or another location determination device or sensor), the AP algorithm executing on the drug delivery device 202 may facilitate entry into the hypoglycemia protect mode of operation by alerting the user to the detected conditions where entry into the hypoglycemia protect mode of operation may be desired but has not occurred simply due to user error (e.g., the user forgot to enter the mode of operation). For example, the controller 221 of the drug delivery device 202 may upon execution of the AP application implement techniques that detect increased activity by the user (e.g., detects the user exercising) and/or detects locations where past increased levels of activity typically occur (e.g., recognizing locations such as a gym, a jogging trail or track, a swimming pool, a bike trail, a golf course, ice skating arena, soccer field, baseball field, football field, other sports field, beach, or the like as locations where the user typically exercises).

Techniques implemented by the drug delivery device 202, including during configuration of the drug delivery device 202, may enable the following parameters to be monitored and included with of the inputs associated with an activity level of a user received by the controller 221:

An "IncreasedActivityDetectionFlag"—allows higher activity to be automatically detected An "AllowLocationDetectionFlag"—allows the user to add locations associated with increased activity levels or for the locations to be automatically detected and stored for reference An "AllowAutoEntryInHypoProtectModeFlag"—allows the drug delivery device 202 to automatically enter the hypoglycemia protect mode of operation In addition, the AP application of the drug delivery device 202 may provide alerts to the user—for example, audible, tactile (e.g., vibrational), and/or visual alerts or similar alerts through the management device 206 or the user interface 227—to remind the user to enter into the hypoglycemia protect mode of operation if current activity levels of the user increase and/or predicted increased activity is expected.

Although some of the examples referenced the controller 221 of the wearable drug delivery device 202 performing some or all of the processes described in the foregoing examples, the disclosed subject matter should not be limited. For example, the described processes may also be performed by the processor 261 of the management device 206 or the processor 241 of the blood glucose sensor 204. Alternatively, some or all of the processes described in the foregoing examples may be distributed among the various processors or controllers, such as 261, 241 and 221 with information shared over the wired communication links 277, 278, 279 or wireless communication links 28, 288, 289.

The techniques described herein for providing an activity mode, hyperglycemia protect mode, or a hypoglycemia protect mode as described herein for a drug delivery system (e.g., the systems 100, 200 or any components thereof) may be implemented in hardware, software, or any combination thereof. Any component as described herein may be implemented in hardware, software, or any combination thereof. For example, the systems 100 and 200 or any components thereof may be implemented in hardware, software, or any combination thereof. Software related implementations of the techniques described herein may include, but are not limited to, firmware, application specific software, or any other type of computer readable instructions that may be executed by one or more processors. Hardware related implementations of the techniques described herein may include, but are not limited to, integrated circuits (ICs), application specific ICs (ASICs), field programmable arrays (FPGAs), and/or programmable logic devices (PLDs). In some examples, the techniques described herein, and/or any system or constituent component described herein may be implemented with a processor executing computer readable instructions stored on one or more memory components.

Some examples of the disclosed devices may be implemented, for example, using a storage medium, a computer-readable medium, or an article of manufacture which may store an instruction or a set of instructions that, if executed by a machine (i.e., processor or controller), may cause the machine to perform a method and/or operation in accordance with examples of the disclosure. Such a machine may include, for example, any suitable processing platform, computing platform, computing device, processing device, computing system, processing system, computer, processor, or the like, and may be implemented using any suitable combination of hardware and/or software. The computer-readable medium or article may include, for example, any suitable type of memory unit, memory, memory article, memory medium, storage device, storage article, storage medium and/or storage unit, for example, memory (including non-transitory memory), removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, programming code, and the like, implemented using any suitable high-level, low-level, object-oriented, visual, compiled and/or interpreted programming language. The non-transitory computer readable medium embodied programming code may cause a processor when executing the programming code to perform functions, such as those described herein.

Certain examples of the present disclosed subject matter were described above. It is, however, expressly noted that the present disclosed subject matter is not limited to those examples, but rather the intention is that additions and modifications to what was expressly described herein are also included within the scope of the disclosed subject matter. Moreover, it is to be understood that the features of the various examples described herein were not mutually exclusive and may exist in various combinations and permutations, even if such combinations or permutations were not made express herein, without departing from the spirit and scope of the disclosed subject matter. In fact, variations, modifications, and other implementations of what was described herein will occur to those of ordinary skill in the art without departing from the spirit and the scope of the disclosed subject matter. As such, the disclosed subject matter is not to be defined only by the preceding illustrative description.

Program aspects of the technology may be thought of as "products" or "articles of manufacture" typically in the form of executable code and/or associated data that is carried on or embodied in a type of machine readable medium. Storage type media include any or all of the tangible memory of the computers, processors or the like, or associated modules thereof, such as various semiconductor memories, tape drives, disk drives and the like, which may provide non-transitory storage at any time for the software programming. It is emphasized that the Abstract of the Disclosure is provided to allow a reader to quickly ascertain the nature of the technical disclosure. It is submitted with the understanding that it will not be used to interpret or limit the scope or meaning of the claims. In addition, in the foregoing Detailed Description, various features are grouped together in a single example for streamlining the disclosure. This method of disclosure is not to be interpreted as reflecting an intention that the claimed examples require more features than are expressly recited in each claim. Rather, as the following claims reflect, inventive subject matter lies in less than all features of a single disclosed example. Thus, the following claims are hereby incorporated into the Detailed Description, with each claim standing on its own as a separate example. In the appended claims, the terms "including" and "in which" are used as the plain-English equivalents of the respective terms "comprising" and "wherein," respectively. Moreover, the terms "first," "second," "third," and so forth, are used merely as labels and are not intended to impose numerical requirements on their objects.

The foregoing description of example examples has been presented for the purposes of illustration and description. It is not intended to be exhaustive or to limit the present disclosure to the precise forms disclosed. Many modifications and variations are possible in light of this disclosure. It is intended that the scope of the present disclosure be limited not by this detailed description, but rather by the claims appended hereto. Future filed applications claiming priority to this application may claim the disclosed subject matter in a different manner and may generally include any set of one or more limitations as variously disclosed or otherwise demonstrated herein.

The invention claimed is:

1. A wearable drug delivery device, comprising:
   a reservoir configured to store a liquid drug;
   a pump mechanism coupled to the reservoir and operable to expel the stored liquid drug from the reservoir;
   an inertial measurement unit operable to detect an activity level of a user; and
   a controller communicatively coupled to the pump mechanism and the inertial measurement unit, wherein the controller is operable to:
      receive an input from the inertial measurement unit, wherein the input indicates one or more measurements of motion;
      determine, from the received input, an activity level change;
      automatically initiate an activity mode of operation based on the determined activity level change exceeding an activity mode threshold;
      based on the determined activity level change, modify an amount of the liquid drug to be delivered by the pump mechanism; and
      output a signal to the pump mechanism actuating delivery of the modified amount of the liquid drug.

2. The wearable drug delivery device of claim 1, wherein the controller is further operable to receive a selection of the activity mode of operation.

3. The wearable drug delivery device of claim 1, further comprises:
   a GPS device or a communication device with access to Wi-Fi location services.

4. The wearable drug delivery device of claim 3, wherein the controller is further operable to:
   receive a location associated with the wearable drug delivery device;
   obtain locations of physical activity from a memory;
   compare the received location to locations of physical activity; and
   based on a result of the comparison, initiate activity mode.

5. The wearable drug delivery device of claim 1, wherein the controller is operable to:
   automatically enter the activity mode of operation based on a determined location of the user.

6. The wearable drug delivery device of claim 1, further comprising:
   a user interface communicatively coupled to the controller, wherein the user interface is operable to:
      provide an input selecting the activity mode of operation.

7. The wearable drug delivery device of claim 6, wherein the controller is operable to:
   generate an alert via the user interface requesting the input selecting the activity mode of operation.

8. A non-transitory computer readable medium embodied with programming code executable by a processor, and the processor when executing the programming code is operable to perform functions, including functions to:
   receive inputs associated with an activity mode;
   evaluate the received inputs with reference to activity mode thresholds;
   determine whether the evaluated inputs exceed at least one activity mode threshold of the activity mode thresholds;
   in response to the evaluated inputs exceeding the at least one activity mode threshold, initiate the activity mode;
   based on initiation of the activity mode, adjust parameters of a diabetes treatment plan; and
   actuate delivery of the liquid drug via a pump mechanism according to the adjusted parameters of the diabetes treatment plan.

9. The non-transitory computer readable medium of claim 8, further embodied with programming code executable by the processor, and the processor when executing the programming code is operable to evaluate the received inputs with reference to activity mode thresholds by performing functions to:
   retrieve the activity mode thresholds from a memory;
   determine a duration of an indication of physical activity;
   compare the determined duration of the indication of physical activity to a default duration value from among the retrieved activity mode thresholds;
   based on a result of the comparison, indicate that the duration of the indication of physical activity exceeds an activity mode threshold for duration of physical activity; and
   output an instruction to initiate activity mode.

10. The non-transitory computer readable medium of claim 9, wherein the activity mode thresholds are based on:
    user history accumulated over days, months or years, user preference settings, or
    clinical information based on an age, a weight, or a height of a user.

11. The non-transitory computer readable medium of claim 8, further embodied with programming code executable by the processor, and the processor when executing the programming code is operable to receive inputs associated with the activity mode by performing functions to:

access scheduling information related to events or physical activity; and identify events and scheduled physical activity that a user is participating for evaluation.

12. The non-transitory computer readable medium of claim 8, wherein, when the programming code is executed by the processor, the processor is operable, upon entering hyperglycemia protect mode, to perform further functions, including functions to:

receive a location associated with a wearable drug delivery device;

obtain locations of physical activity from a memory;

compare the received location to the obtained locations of physical activity; and based on a result of the comparison indicating that the location associated with the wearable drug delivery device is substantially the same as a location in the locations of physical activity obtained from the memory, indicate that an activity mode threshold has been exceeded.

13. The non-transitory computer readable medium of claim 8, further embodied with programming code executable by the processor, and the processor when executing the programming code is operable to perform further functions to:

receive an input indicating a location of a wearable drug delivery device;

obtain location information related to physical activity;

compare the received input indicating the location of the wearable drug delivery device; and based on a result of the comparison, enter a hypoglycemia protect mode.

14. The non-transitory computer readable medium of claim 8, wherein the processor is operable, when the programming code is executed by the processor, to perform further functions, including functions to:

generate an alert via a user interface requesting an input to initiate the activity mode; and receive an input via a user interface indicating the initiation of the activity mode of operation.

15. The non-transitory computer readable medium of claim 8, further embodied with programming code executable by the processor, and the processor when executing the programming code is operable to perform further functions to:

process blood glucose measurements; and based on an indication that the blood glucose measurements are increasing toward exceeding a maximum blood glucose set point, enter hyperglycemia protect mode.

16. The non-transitory computer readable medium of claim 15, wherein, when the programming code is executed by the processor, the processor is operable, upon entering hyperglycemia protect mode, to perform further functions, including functions to:

relax liquid drug delivery constraints to reduce an amount of the liquid drug to be delivered;

lower thresholds for triggering hyperglycemia alarms; and reduce a blood glucose set point.

17. The non-transitory computer readable medium of claim 8, further embodied with programming code executable by the processor, and the processor when executing the programming code is operable to perform further functions to:

process blood glucose measurements; and based on an indication that the blood glucose measurements are decreasing toward a minimum blood glucose set point, enter hypoglycemia protect mode.

18. The non-transitory computer readable medium of claim 17, wherein, when the programming code is executed by the processor, the processor is operable, upon entering hypoglycemia protect mode, to perform further functions, including functions to:

reduce maximum liquid drug delivery limits;

reduce an amount of liquid drug indicated as being delivered in basal inputs provided for processing of a dosage of the liquid drug; and increase a minimum blood glucose set point.

19. The non-transitory computer readable medium of claim 17, wherein, when the programming code is executed by the processor, the processor is operable, upon entering hyperglycemia protect mode, to perform further functions, including functions to:

generate a prompt requesting a user to ingest carbohydrates for presentation on a user interface of a wearable drug delivery device.

20. A wearable drug delivery device, comprising:

a reservoir configured to store a liquid drug;

a pump mechanism coupled to the reservoir and operable to expel the stored liquid drug from the reservoir;

an inertial measurement unit operable to detect an activity level of a user; and a controller communicatively coupled to the pump mechanism and the inertial measurement unit, wherein the controller is operable to:

automatically enter an activity mode of operation based on a determined location of the user;

receive an input from the inertial measurement unit, wherein the input indicates one or more measurements of motion;

determine, from the received input, an activity level change;

based on the determined activity level change, modify an amount of the liquid drug to be delivered by the pump mechanism; and output a signal to the pump mechanism actuating delivery of the modified amount of the liquid drug.

\* \* \* \* \*